US008367387B2

(12) United States Patent
Pecyna et al.

(10) Patent No.: US 8,367,387 B2
(45) Date of Patent: Feb. 5, 2013

(54) FUNGAL PEROXYGENASES AND METHODS OF APPLICATION

(75) Inventors: Marek Jan Pecyna, Halle (DE); Kirk Matthew Schnorr, Holte (DK); René Ullrich, Drebkau (DE); Katrin Scheibner, Jena (DE); Martin Gunter Kluge, Zittau (DE); Martin Hofrichter, Zittau (DE)

(73) Assignee: Novozymes A/S, Bagsvaerd (DK)

( * ) Notice: Subject to any disclaimer, the term of this patent is extended or adjusted under 35 U.S.C. 154(b) by 198 days.

(21) Appl. No.: 12/532,870

(22) PCT Filed: Mar. 31, 2008

(86) PCT No.: PCT/EP2008/053798
§ 371 (c)(1),
(2), (4) Date: Jul. 15, 2010

(87) PCT Pub. No.: WO2008/119780
PCT Pub. Date: Oct. 9, 2008

(65) Prior Publication Data
US 2010/0279366 A1 Nov. 4, 2010

(30) Foreign Application Priority Data
Mar. 30, 2007 (DE) .......... 10 2007 016 139

(51) Int. Cl.
C12N 9/08 (2006.01)
C12N 9/02 (2006.01)
C12N 1/20 (2006.01)
C12N 1/00 (2006.01)
C12P 17/12 (2006.01)
C12P 21/00 (2006.01)
C12P 19/34 (2006.01)
C07H 21/04 (2006.01)
C07K 1/00 (2006.01)

(52) U.S. Cl. ....... 435/192; 435/189; 435/122; 435/69.1; 435/91.1; 435/252.3; 435/254.11; 536/23.1; 536/23.2; 530/350

(58) Field of Classification Search .................. 435/192, 435/189, 122, 69.1, 91.1, 252.3, 254.11; 536/23.1, 23.2; 530/350
See application file for complete search history.

(56) References Cited

FOREIGN PATENT DOCUMENTS
DE 103 32 065 1/2005
WO WO 2006/034702 4/2006

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Ullrich et al., "Novel haloperoxidase from the agaric basicjiomycete Agrocybe aegerita oxidizes aryl alcohols and aldehydes", Applied and Environmental Microbiology, vol. 70, No. 8, pp. 4575-4581 (2004).
Ullrich and Hofrichter, "The haloperoxidase of the agaric fungus Agrocybe aegerita hydroxylates toluene and naphthalene", FEBS Letters, vol. 579, No. 27, pp. 6247-6250 (2005).
Kluge et al., "Spectrophotometric assay for detection of aromatic hydroxylation catalyzed by fungal haloperoxidase—peroxygenase", Applied Microbiology and Biotechnology, vol. 75, pp. 1473-1478 (2007).
Anh et al., "The Coprophilous Mushroom Coprinus radians Secretes a Haloperoxidase that Catalyzes Aromatic Peroxygenation", Applied and Environmental Microbiology, vol. 73, No. 17, pp. 5477-5485 (2007).
Colby et al., "The soluble methane monooxygenase of Methylococcus capsulatus (Bath)", Biochemical Journal, vol. 165, pp. 395-402 (1977).
Fetzner, "Bacterial degradation of pyridine, indole, quinoline, and their derivatives under different redox conditions", Applied Microbiology and Biotechnology, vol. 49, pp. 237-250 (1998).
Hofrichter et al. "Heme-thiolate haloperoxidases: versatile biocatalysts with biotechnological and environmental significance", Applied Microbiology and Biotechnology, vol. 71, No. 3, pp. 276-288, (2006).
Search Report issued in corresponding international application No. PCT/EP2008/053798 dated Jan. 19, 2009.

* cited by examiner

Primary Examiner — Ganapathirama Raghu
(74) Attorney, Agent, or Firm — Jason I. Garbell

(57) ABSTRACT

The invention relates to polypeptides having peroxygenase activity and compositions comprising such polypeptides, their encoding polynucleotides, expression vectors and recombinant host cells comprising such polynucleotides or vectors, methods of producing the polypeptides, as well as methods of application and uses thereof, including a process for enzymatic, regioselective oxygenation of N-heterocycles of the general formula (I) to the corresponding N-oxides of the formula (II), by converting N-heterocycles of the formula (I) with a peroxidase polypeptide in the presence of at least one oxidizing agent in a one-stage reaction process.

15 Claims, 6 Drawing Sheets

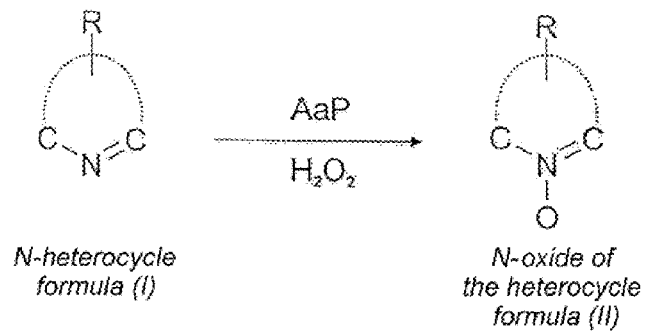
Figure 1. General scheme of the conversion of heterocycles by the enzyme AaP or similar peroxygenases of the first aspect of the invention (the dotted curve is intended to symbolize a ring system).
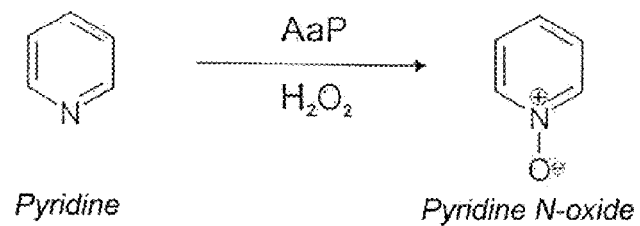
Figure 2. Formula scheme according to example 6.

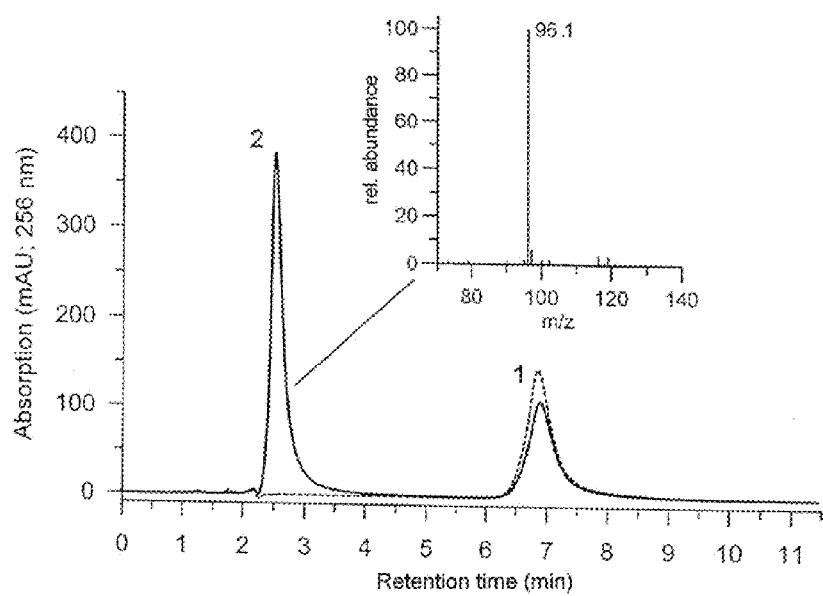
Figure 3. HPLC elution profile (256 nm) of the conversion of pyridine (1) by AaP to pyridine N-oxide (2) of Example 1; insert: mass spectrum of pyridine N-oxide.

```
Agrocybe_AaP1    -----MKYFSLFPTLIFA----AGVIAFPSHASLAGLSEQELDEIIPTLEIREPTQPPGPPE
Agrocybe_AaP2    -----MKYFPLFPTLVFA----ARVVAFPAYASLAGLSQQELDAIIPTLEAREPGLPPGPLE
L_bicolor        ----MARLTFLAAIALALSSTTVLAFPSYGSLAGLSEAELDRIIPLLEARNAGPPPGPLK
C_cinereus_1     MISTSKHLFVLLPLFIVSHLSLVLGFPAYASLGGLTERQVEEYTSKLPIVFPPPPEPIK
C_cinereus_2     ----MVSCKLPLPLLTLAIALANVNAFPAYQSLGGLSKRQLETIIPGLPVVNPGPPGPLA
C_cinereus_3     MNGLFATVKLALVTLLASQSQFANAFPAWQSLGGLSERQLDEVMPMLKHRVPPPPGPPA
C_cinereus_4     ---------------------------------------------MLKPRVPPPPGPLA
C_radians        ------------------------------------------------------------
Consensus                                                             PPP---E
                                                                       **

Agrocybe_AaP1    DTSAKLVNDKDHPWKPLRPG-DIRGPCPGLNTLASHGYLPRNGVATPAQIINAVQEGFNM
Agrocybe_AaP2    NSSAKIVNDEAHPWKPLRPG-DIRGPCPGLNTLASHGYLPRNGVATPVQIINAVQEGLNF
L_bicolor        NTSTKLVNDKNHPWKPLGYG-DIRGPCPGLNTLASHGWLPRNGIATPAQIVNAVQEGFNM
C_cinereus_1     DPWLKLVNDRAHPWRPLRRG-DVRGPCPGLNTLASHGYLPRDGVATPAQIITAVQEGFNM
C_cinereus_2     DSTLKLVNDAAHPYQAPRPHLDHRGPCPGLNTLANHGYLPRSGIATPAQIVQAVMEGFNM
C_cinereus_3     FTGAKLVNDKAHPFKPLKKG-DVRGPCPGLNTLASHGYLPRNGVASPSQIIDAVQEGFNM
C_cinereus_4     FNGTKLVNDEDHPFMPPRKG-DARGPCPGLNTLASHGYLPRNGIATPAQIINAVQEGFNM
C_radians        YVGPKLVNDADHPWEPLRPG-DIRGPCPGLNTLASHGYLPRNGVATPAQIINAIVEGFNF
Consensus             *  ******  *: .  *  ******************.**:****. *: ** :****:
                                                                      (cont. next page)
```

Figure 4A. Alignment of the 8 peroxygenase amino acid sequences shown in SEQ ID NO's: 2, 4, 6, 8, 10, 12, 14, and 19, respectively; continued on next page.

```
Agrocybe_AaP1      DNSVALFATYEAHLMVGNLLTDLLSIGRKTPLTG-PDLPPPANIGGLSEHGL-FEGDASM
Agrocybe_AaP2      DNQAAVFATYAAHLVDGNLITDLLSIGRKTRLTG-PDPPPASVGGLNEHGTEFEGDASM
L_bicolor          GNDLAVFVTYAAHLVDGNQVTDLLSIGGKTPQTG-PDPPAPAIVGGLNTHAV-FEGDASM
C_cinereus_1       EYGIATFVTYAAHLVDGNPLTNLISIGGKTRKTG-PDPPPPAIVGGLNTHAV-FEGDASM
C_cinereus_2       ENTFAKFVTYAAFLVDGNPITNLMSIGGKTWRTGIIEPPPPAIVGGLNTHAV-FEGDTSM
C_cinereus_3       ENELARFTTYVAHLVDGNLVTDLLSIGEKTRKTG-PDPPPPAIVGGLNNHGT-FEGDASL
C_cinereus_4       ENEIARFTTYTAHLMDGNLVTDLLSIGPKTPKTG-PDPPPPAIVGGLNNHGT-FEGDASL
C_radians          NYEGAVFVTYEAHIVDGNLVTDLLSIGGKTNLTG-EDTGAPAIIGGLNTHSV-FEGDASM
Consensus                * *.*** * *.  :  *:.:*:** .**            *  .  *****:*:.

Agrocybe_AaP1      TRGDAFFGNNDEFNEELFQQFIDYSNRFGGGYYNLTVAVELRFKRIQDSIATNPEFNFVS
Agrocybe_AaP2      TRGDAFFGNNHDFNETLFEQLVDYSNRFGGGKYNLTVAGELRFKRIQDSIATNPNFSFVD
L_bicolor          TRGDAFFGDNHSFNETQFDEFSAFSNKFGGGYYNLSVAAEFRWQRIQESIATNPNFSLIS
C_cinereus_1       TRGDFHLGDNFNFNQTLWEQFKDYSNRYGGGRYNLTAAAELRWARIQQSMATNGQFDFTS
C_cinereus_2       TRGDFHFGDNHSFNQTLFDQFVEYSNTHGGGFYNLTAATELRYQRIQQSIATNPEMSFVS
C_cinereus_3       TRGDAFFGDNHNFNQELFDQFKNFSAVYGNGFFNMTVAGELRFHRIQQSIATNPEFSLVG
C_cinereus_4       SRADAFFGDNHSFDQELFDQFRNFSAIYGNGFFNMTVAAELRFHRIQQSIATNPEFSFAG
C_radians          TRDDFHFGDNHSFNQTLFDQFVEYSNTYGGGFYNQEVAGHLRRRIEQSIATNPEFDFTS
Consensus          :*.* *  :.:.*:.* . .: ..*  ..*  *   *.   *  **:*:***  *.  .

[    Motif I    ]      [    Motif II    ]
                                                             [   Motif III  ]
                                                                      [   Motif IV   ]
```

Figure 4B. Alignment of the 8 peroxygenase amino acid sequences shown in SEQ ID NO's: 2, 4, 6, 8, 10, 12, 14, and 19, respectively.

```
Agrocybe_AaP1    PRFFAAYGESVAPNNFFVDGRK------DDGHLDMDAARGFFQFGRMPDGFFRPNGTKG--
Agrocybe_AaP2    FRFFTAYGETTFPANLFVDGRR------DDGQLDMDAARSFFQFSRMPDDFFRAPSPRS--
L_bicolor        PRYFTAYAESVFPLVFFVDGRV------SDGRLSLPNARGFFQNSQMPKDFFRPNQSIGLN
C_cinereus_1     PRYFTAYAESVFPINFFTDGRLFTSNTTAPGPDMDSALSFFRDHRYPKDFHRAPVPSG---
C_cinereus_2     PRWFTAIL------------------------LQDEKFPDDFHRAPGPFS--
C_cinereus_3     LRHLTAYAEASFPSLFFVDGRK--TGAEAGQLDMATAESFFRDMMYPPDFFRPAAPV---
C_cinereus_4     LRHITAYAEASFPPIFFVDGRK--TGAEAGQLDMAAAESFFKHMMYPPDFHRPAEPV---
C_radians        PRFFTAFAESSFPYSFFVDGRI---TE-RPGGLSMENATLFFRDHKMPDDFWRAPEPTG--
Consensus        *   :  :*                    .            * .* *:*.   .
                                                            [Motif V]

Agrocybe_AaP1    --NAGLDDVVRAHPVQP-GRNL-GRVNSYTHDPTSADFTTPCLLYENFANKTVTALYPNP
Agrocybe_AaP2    --GTGVEVVIQAHPMQP-GRNV-GKINSYTVDPTSSDFSTPCLMYEKFVNITVKSLYPNP
L_bicolor        EIGDGISAIASAHPIAP-GKNE-G-VGNYVLDPTSADFDHFCLLYINFVNQTVKSLYPNP
C_cinereus_1     --ARGLDVVAAAYPIQP-GYNADGKVNNYVLDPTSADFTKFCLLYENFVLKTVKGLYPNP
C_cinereus_2     --FEGLGYLVTRRPMPP-GRNV-GGVDNYVPDPNSADFNSFCKMYEDFVNDIVVALYPNP
C_cinereus_3     --AGDAGAIFLAHPFQP-GRNV-GGVNNFTVDDSLGSLLDFCGFYENFVNKTLKALYPNP
C_cinereus_4     --NSDAQAVFEVHPFQP-GRNV-GGVNNYTVDESLGGLLDFCGFYENFVNKTIKGLYPNP
C_radians        --GLNVLDIYRASGSPPAGRNV-NGTNTFTPDPNSADFDNPCELYYDYVNRIVKSLYPNP
Consensus              .     *  *     * *   .  :. .: .     :  .:.  . .:*****
                                                            [ Motif VI
                                                            (cont. next page)
```

Figure 4C. Alignment of the 8 peroxygenase amino acid sequences shown in SEQ ID NO's: 2, 4, 6, 8, 10, 12, 14, and 19, respectively, with a consensus indication (continued on next page).

```
Agrocybe_AaP1   KGQLRRAIKANLHFLFLAINRTVG------CAEVFPYGRD--
Agrocybe_AaP2   TVHVRKALNTNLDFFFQGVAAG-------CTQVFPYGRD--
L_bicolor       KGVLLDALKRNLNNFYGPLNGSD------CEQIFPYGK---
C_cinereus_1    KGFLRKALETNLEYFYQSFPGSGG-----CPQVFPWGKSD-
C_cinereus_2    TGLLRRNLIKNLEYFWTGMFDPA------CTEVKPYGTL--
C_cinereus_3    KGVLRRNLNINLQFFEESLPKDESGTPVCTQVFPYGRN---
C_cinereus_4    TGVLKRNLNINLDFLFEALPKAGDGSQPCTQVFPYGHD---
C_radians       TGILRDNLNIALGHVFDSMDFGD------CEQLFPYGR---
Consensus        .  :  *  :   ..                *  *:*
                 -- Motif VI ]
```

Figure 4D. Alignment of the 8 peroxygenase amino acid sequences shown in SEQ ID NO's: 2, 4, 6, 8, 10, 12, 14, and 19, respectively, with a consensus indication.

FUNGAL PEROXYGENASES AND METHODS OF APPLICATION

CROSS-REFERENCE TO RELATED APPLICATIONS

This application is a 35 U.S.C. 371 national application of PCT/EP2008/053798/filed 31 Mar. 2008, which claims priority or the benefit under 35 U.S.C. 119 of German patent application no. 10 2007 016 139.7 filed 30 Mar. 2007, the contents of which are fully incorporated herein by reference.

SEQUENCE LISTING AND DEPOSITED MICROORGANISMS

Sequence Listing

The present invention comprises a sequence listing in computer readable form. The computer readable form is incorporated herein by reference.

Deposit of Biological Material

The following biological material has been deposited under the terms of the Budapest Treaty with the DSMZ (Deutsche Sammlung von Mikroorganismen and Zellkulturen GmbH) and given the following accession number. Two *Escherichia coli* clones, each containing a standard plasmid comprising the cDNA gene encoding the AaP1 and AaP2 peroxygenase enzymes of *Agrocybe aegerita* TM-A1-K shown in SEQ ID NO's 1/2 and 3/4, respectively.

| Deposit | Accession Number | Date of Deposit |
|---|---|---|
| E. coli NN049991 (AaP1) | DSM 21289 | 14 Mar. 2008 |
| E. coli NN049992 (AaP2) | DSM 21290 | 14 Mar. 2008 |

The strains have been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

FIELD OF THE INVENTION

The invention relates to polypeptides having peroxygenase activity and compositions comprising such polypeptides, their encoding polynucleotides, expression vectors and recombinant host cells comprising such polynucleotides or vectors, methods of producing the polypeptides, as well as methods of application and uses thereof, including a process for enzymatic, regioselective oxygenation of N-heterocycles of the general formula (I) to the corresponding N-oxides of the formula (II), by converting N-heterocycles of the formula (I) with a peroxidase polypeptide in the presence of at least one oxidizing agent in a one-stage reaction process.

BACKGROUND OF THE INVENTION

A haloperoxidase peroxygenase denoted AaP from the agaric basidiomycete strain *Agrocybe aegerita* (strain TM-A1) was found to oxidize aryl alcohols and aldehydes. The AaP peroxygenase was purified from *A. aegerita* TM A1 by several steps of ion chromatography and SDS-PAGE, the molecular weight was determined and the N-terminal 14 amino acid sequence was determined after 2-D electrophoresis but the encoding gene was not isolated (Ullrich et al., 2004, Appl. Env. Microbiol. 70(8): 4575-4581).

WO 2006/034702 A1 discloses methods for the enzymatic hydroxylation of non-activated hydrocarbons, such as, naphtalene, toluol and cyclohexane, using the AaP peroxygenase enzyme of *Agrocybe aegerita* TM A1. This is also described in Ullrich and Hofrichter, 2005, FEBS Letters 579: 6247-6250.

DE 103 32 065 A1 discloses methods for the enzymatic preparation of acids from alcohols through the intermediary formation of aldehydes by using the AaP peroxygenase enzyme of *Agrocybe aegerita* TM A1.

A method was reported for the rapid and selective spectrophotometric direct detection of aromatic hydroxylation by the AaP peroxygenase (Kluge et al., 2007, Appl Microbiol Biotechnol 75: 1473-1478).

A second peroxygenase capable of aromatic peroxygenation was isolated from the coprophilous fungus *Coprinus radians* and characterized, the N-terminal 16 amino acids were identified and aligned with the N-terminal 14 amino acids of the AaP enzyme of the *A. aegerita* strain earlier published; but the encoding gene was not isolated (Anh et al., 2007, Appl Env Microbiol 73(17): 5477-5485).

It is well-known that a direct regioselective introduction of oxygen functions (oxygenation) into organic molecules constitutes a problem in chemical synthesis. It is particularly difficult to catalyse the selective N-oxygenation of aromatic heterocycles of the pyridine type. The products, heterocyclic N-oxides, are important intermediates in a wide variety of different syntheses and are often biologically active. In addition, they function as protecting groups, oxidizing agents, ligands in metal complexes and specific catalysts.

The chemical oxygenation of pyridine, derivatives thereof and other N-heterocycles is relatively complex, requires aggressive/toxic chemicals/catalysts and leads to a series of undesired by-products (e.g. 2-, 3- and/or 4-hydroxypyridine derivatives) and low isomer yields. According to the literature, pyridine N-oxide can be chemically synthesized from pyridine using the following starting compounds among others:

hydrogen peroxide (30%), acetic acid and pyridine (80° C. in pyridine/water)

phosphotungstic acid on silicon dioxide and pyridine (80° C. in pyridine)

tungstic acid salts, hydrogen peroxide (30%) and pyridine (80° C. in pyridine)

organic hydrotrioxides and pyridine (−80 to −60° C. in pyridine)

hydrogen peroxide, manganese tetrakis(2,6-chlorophenyl) porphyrin (25° C. in dichloroethane)

dimethyloxirane and pyridine (0° C., in dichloroethane)

perfluoro(cis-2,3-dialkyloxaziridine) and pyridine (25° C. in pyridine).

Oxygenation reactions on heterocyclic nitrogen atoms are usually based on generation, in the presence of electron donors and molecular oxygen ($O_2$) or a peroxide/trioxide (R—OOH, R—OOOH), by a catalyst, of a reactive oxygen species which attacks the nitrogen directly. These highly reactive oxygen species have only limited regioselectivity. For this reason, the yields in chemical N-oxygenations are low, and they lead to undesired by-products and require a complicated operation.

It is known that an intracellular enzyme, methane monooxygenase (MMO, EC 14.13.25), converts pyridine to pyridine N-oxide in an unspecific side reaction. The MMO enzyme consists of several protein components and is formed by methylotrophic bacteria (e.g. *Methylococcus capsulatus*); it requires complex electron donors such as NADH or NADPH, auxiliary proteins (flavin reductases, regulator protein) and molecular oxygen ($O_2$). The natural substrate of MMO is methane, which is oxidized to methanol.

As a particularly unspecific biocatalyst, MMO oxygenates/hydroxylates, as well as methane, a series of further substrates such as n-alkanes and their derivatives, cycloalkanes, aromatics, carbon monoxide and heterocycles. The latter and pyridine in particular are, however, converted only with very low rates; the specific activity with respect to pyridine is 0.029 unit $mg^{-1}$ of protein (Colby et al. 1977: *The soluble methane monooxygenase of Methylococcus capsulatus. Biochem. J.* 165: 395-402). Utilization of the enzyme in biotechnology is currently not possible, since it is difficult to isolate, like most intracellular enzymes, it is of low stability, and the cosubstrates required are relatively expensive.

Pyridine-degrading bacteria such as *Rhodococcus* spp. or *Arthrobacter* spp. do not possess any enzyme which generates pyridine N-oxide, but rather utilize enzymes which hydroxylate the pyridine ring at the carbon (rare) or reduce particular bonds of the ring (common) and thus initiate the degradation (Fetzner, S., 1998: *Bacterial degradation of pyridine, indole, quinoline, and their derivatives under different redox conditions. Appl. Microbiol. Biotechnol.* 49: 237-250).

SUMMARY OF THE INVENTION

In a first aspect, the invention relates to an isolated polypeptide, which is preferably recombinantly produced, having peroxygenase activity, selected from the group consisting of:

(a) a polypeptide comprising an amino acid sequence having at least 60% identity, preferably at least 65%, 70%, 75%, 80%, 85%, 90%, 95%, 97%, or 98% identity to the polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19;

(b) a polypeptide encoded by a polynucleotide that hybridizes under at least low, medium, medium-high, or high stringency conditions with (i) the mature polypeptide coding sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; (ii) the cDNA sequence contained in or the genomic DNA sequence comprising the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; or (iii) a full-length complementary strand of (i) or (ii);

(c) a polypeptide encoded by a polynucleotide comprising a nucleotide sequence having at least 60% identity, preferably at least 65%, 70%, 75%, 80%, 85%, 90%, 95%, 97%, or 98% identity to the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17;

(d) a polypeptide comprising one or more of the following motifs, preferably comprising two or more, three or more, four or more, five or six of the following motifs:

| | | |
|---|---|---|
| Motif I: | [FL]XX[YF]S[AN]X[FHY]G[GN]GX[YF]N | (SEQ ID NO: 40) |
| Motif II: | G[GN]GX[YF]NXX[VA]AX[EH][LF]R | (SEQ ID NO: 41) |
| Motif III: | RXXRI[QE][DEQ]S[IM]ATN | (SEQ ID NO: 42) |
| Motif IV: | S[IM]ATN[PG][EQN][FM][SDN][FL] | (SEQ ID NO: 43) |
| Motif V: | P[PDK][DG]F[HFW]R[AP] | (SEQ ID NO: 44) |
| Motif VI: | [TI]XXXLYPNP[TK][GV]; | (SEQ ID NO: 45) | and (e) a variant comprising a substitution, deletion, and/or insertion of one or several amino acids of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19.

In a second aspect, the invention relates to an isolated polynucleotide comprising a nucleotide sequence that encodes the polypeptide of the first aspect.

A third aspect of the invention relates to a nucleic acid construct comprising the polynucleotide of the second aspect operably linked to one or several control sequences that direct the production of the polypeptide in an expression host.

In a fourth aspect the invention relates to a recombinant expression vector comprising the nucleic acid construct of the third aspect.

The fifth aspect of the invention relates to a recombinant host cell comprising the nucleic acid construct of claim the third aspect or the expression vector of the fourth aspect.

A sixth aspect of the invention relates to a method of producing the polypeptide of the first aspect, comprising: (a) cultivating a cell, which in its wild-type form produces the polypeptide, under conditions conducive for production of the polypeptide; and (b) recovering the polypeptide.

A seventh aspect of the invention relates to a method of producing the polypeptide of the first aspect, comprising: (a) cultivating a host cell comprising a nucleic acid construct comprising a nucleotide sequence encoding the polypeptide under conditions conducive for production of the polypeptide; and (b) recovering the polypeptide.

An eighth aspect of the invention relates to a method of producing a mutant of a parent cell, comprising disrupting or deleting a nucleotide sequence encoding the polypeptide of the first aspect, which results in the mutant producing less of the polypeptide than the parent cell.

A ninth aspect of the invention relates to a mutant cell produced by the method of the eighth aspect.

In a tenth aspect the invention relates to a method of producing a protein, comprising: (a) cultivating the mutant cell the ninth aspect under conditions conducive for production of the protein; and (b) recovering the protein.

An eleventh aspect of the invention relates to a method of producing a polynucleotide comprising a mutant nucleotide sequence encoding a polypeptide having peroxygenase activity, comprising: (a) introducing at least one mutation into the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, wherein the mutant nucleotide sequence encodes a polypeptide comprising or consisting of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14 or SEQ ID NO:19; and (b) recovering the polynucleotide comprising the mutant nucleotide sequence.

A twelfth aspect of the invention relates to a mutant polynucleotide produced by the method of the eleventh aspect.

In a thirteenth aspect the invention relates to a method of producing a polypeptide, comprising: (a) cultivating a cell comprising the mutant polynucleotide of the twelfth aspect encoding the polypeptide under conditions conducive for production of the polypeptide; and (b) recovering the polypeptide.

A fourteenth aspect of the invention relates to a method of producing the polypeptide of the first aspect, comprising: (a) cultivating a transgenic plant or a plant cell comprising a polynucleotide encoding the polypeptide under conditions conducive for production of the polypeptide; and (b) recovering the polypeptide.

A fifteenth aspect of the invention relates to a nucleic acid construct comprising a gene encoding a protein operably linked to one or both of a first nucleotide sequence encoding a signal peptide comprising or consisting of amino acids −43 to −1 of SEQ ID NO: 2, and a second nucleotide sequence encoding a propeptide comprising or consisting of amino acids 1 to 330 of SEQ ID NO: 2, wherein the gene is foreign to the first and second nucleotide sequences.

In a sixteenth aspect, the invention relates to a recombinant expression vector comprising the nucleic acid construct of the previous aspect.

A seventeenth aspect relates to a recombinant host cell comprising the nucleic acid construct of the previous aspect.

An eighteenth aspect relates to a method of producing a protein, comprising: (a) cultivating the recombinant host cell of the previous aspect under conditions conducive for production of the protein; and (b) recovering the protein.

It is an object of the present invention to perform a process for preparing pyridine N-oxide and other N-heterocycles from the corresponding precursors with a very low level of process technology and apparatus complexity and at the same time with the use of inexpensive cosubstrates. The conversion of the starting compounds shall be effected in very short incubation times, at room temperature and pressure, in an aqueous medium and without increased demands for sterile or semisterile reaction conditions. The reaction products should be isolated with a minimum level of complexity and a complicated separation of different structural isomers shall be dispensed with.

A twentieth aspect of the invention relates to a process for enzymatic, regioselective oxygenation of N-heterocycles of the formula (I) in FIG. 1 to corresponding N-oxides of the formula (II) in FIG. 1, by converting N-heterocycles of the formula (I) in FIG. 1 with a peroxygenase polypeptide as defined in the first aspect in the presence of at least one oxidizing agent in a one-stage reaction process.

In another aspect, the invention relates to a process for enzymatic, regioselective oxygenation of aromatic N-heterocycles of the formula (I) to corresponding N-oxides of the formula (II) by converting an N-heterocycle of the formula (I) with a fungal aromatic haloperoxidase peroxygenase in the presence of at least one oxidizing agent in a one-stage reaction process.

Final aspects of the invention relates to several types of compositions comprising a polypeptide as defined in the first aspect, such as, a detergent composition, a dishwasher detergent composition, a composition for pulp and paper treatment, a composition for water treatment, and a composition for oil treatment.

DRAWINGS

FIG. 1: General formula scheme of the peroxygenase-catalysed conversion of N-heterocycles FIG. 2: Formula scheme according to example 1.

FIG. 3: HPLC elution profile (256 nm) of the conversion of pyridine by AaP with the mass spectrum of the only product, pyridine N-oxide.

FIG. 4: FIGS. 4A-4D show a multiple alignment of the of the 8 peroxygenase amino acid sequences shown in SEQ ID NO's: 2, 4, 6, 8, 10, 12, 14, and 19, respectively, together with a consensus indication and six conserved motifs characteristic of fungal peroxygenases.

DEFINITIONS

Peroxygenase activity: The term "peroxygenase activity" (AaP: E.C. 1.11.1.-) is defined herein as the capability to oxidize a wide variety of compounds including phenols, ABTS [2,2'-azinobis(3-ethylbenzthiazoline-6-sulfonic acid)], aryl alcohols, N-heterocycles of the formula I (see FIG. 1), and aldehydes and inorganic bromide. For purposes of the present invention, peroxygenase activity is determined according to the spectrophotometric procedure described by Kluge et al. (2007, Appl Microbiol Biotechnol 75: 1473-1478).

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the peroxygenase activity of the mature polypeptide of SEQ ID NO: 2, 4, 6, 8, 10, 12, 14, or 19.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having peroxygenase activity that is in its final form following translation and any post-translational modifications, such as N-terminal processing, C-terminal truncation, glycosylation, phosphorylation, etc. In a preferred aspect, the mature polypeptide has the amino acid sequence shown in positions 1 to 330 of SEQ ID NO: 2 based on the N-terminal peptide sequencing data (Ullrich et al., 2004, Appl. Env. Microbiol. 70(8): 4575-4581), elucidating the start of the mature protein of AaP peroxygenase enzyme.

Mature polypeptide coding sequence: The term "mature polypeptide coding sequence" is defined herein as a nucleotide sequence that encodes a mature polypeptide having peroxygenase activity. In a preferred aspect, the mature polypeptide coding sequence is nucleotides 152 to 1141 of SEQ ID NO: 1.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the polypeptide shown in SEQ ID NO: 2, 4, 6, 8, 10, 12, 14, or 19.

Polypeptide fragment: The term "polypeptide fragment" is defined herein as a polypeptide having one or more (several) amino acids deleted from the amino and/or carboxyl terminus of the mature polypeptide of SEQ ID NO: 2, 4, 6, 8, 10, 12, 14, or 19; or a homologous sequence thereof; wherein the fragment has peroxygenase activity.

Subsequence: The term "subsequence" is defined herein as a nucleotide sequence having one or more (several) nucleotides deleted from the 5' and/or 3' end of the mature polypeptide coding sequence of SEQ ID NO: 1, 3, 5, 7, 9, 11, 13, 15, or 17; or a homologous sequence thereof; wherein the subsequence encodes a polypeptide fragment having peroxygenase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA.

These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, 4, 6, 8, 10, 12, 14, or 19; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having peroxygenase activity produced by an organism expressing a modified polynucleotide sequence of the mature polypeptide coding sequence of one of SEQ ID NO: 1, 3, 5, 7, 9, 11, 13, 15, or 17; or a homologous sequence thereof. The modified nucleotide sequence is obtained through human intervention by modification of the polynucleotide sequence disclosed in SEQ ID NO: 1, 3, 5, 7, 9, 11, 13, 15, or 17; or a homologous sequence thereof.

DETAILED DESCRIPTION

A number of fungal peroxygenase genomic DNA's and cDNA's are shown along with the encoded amino acid sequences in the sequence listing of this application:

SEQ ID NO:1 shows a cDNA polynucleotide sequence encoding the AaP1 enzyme from *Agrocybe aegerita*, the amino acid sequence of which is shown in SEQ ID NO:2.

SEQ ID NO:3 shows a cDNA polynucleotide sequence encoding the AaP2 enzyme from *Agrocybe aegerita*, the amino acid sequence of which is shown in SEQ ID NO:4.

SEQ ID NO:5 shows a genomic DNA polynucleotide sequence encoding the peroxygenase enzyme from *Laccaria bicolor*, the amino acid sequence of which is shown in SEQ ID NO:6.

SEQ ID NO:7 shows a cDNA polynucleotide sequence (CC1G_08427) encoding the peroxygenase1 enzyme from *Coprinopsis cinerea okayama* strain 7#130, the amino acid sequence of which is shown in SEQ ID NO:8 (putative protein UNIPROT:A8NAQ8).

SEQ ID NO:9 shows a cDNA polynucleotide sequence (CC1G_10475) encoding the peroxygenase2 enzyme from *Coprinopsis cinerea okayama* strain 7#130, the amino acid sequence of which is shown in SEQ ID NO:10 (putative protein UNIPROT:A8NL34).

SEQ ID NO:11 shows a cDNA polynucleotide sequence (CC1G_08981) encoding the peroxygenase3 enzyme from *Coprinopsis cinerea okayama* strain 7#130, the amino acid sequence of which is shown in SEQ ID NO:12 (putative protein UNIPROT:A8P4U7).

SEQ ID NO:13 shows a cDNA polynucleotide sequence (CC1G_08975) encoding the peroxygenase4 enzyme from *Coprinopsis cinerea okayama* strain 7#130, the amino acid sequence of which is shown in SEQ ID NO:14 (putative protein UNIPROT:A8P4T7).

SEQ ID NO:15 shows a 5'-end partial cDNA polynucleotide sequence encoding part of the peroxygenase enzyme from *Coprinus radians* DSM888 (publicly available from DSMZ, Germany), the partial amino acid sequence of which is shown in SEQ ID NO:16.

SEQ ID NO:17 shows a 3'-end partial cDNA polynucleotide sequence encoding part of the peroxygenase enzyme from *Coprinus radians* DSM888, the partial amino acid sequence of which is shown in SEQ ID NO:18.

SEQ ID NO:19 shows the merged amino acid sequence of the partial sequences in SEQ ID NO's 16 and 18 of the peroxygenase enzyme from *Coprinus radians* DSM888.

In a first aspect, the invention relates to an isolated polypeptide, which is preferably recombinantly produced, having peroxygenase activity, selected from the group consisting of:

(a) a polypeptide comprising an amino acid sequence having at least 60% identity, preferably at least 65%, 70%, 75%, 80%, 85%, 90%, 95%, 97%, or 98% identity to the polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19;

(b) a polypeptide encoded by a polynucleotide that hybridizes under at least low, medium, medium-high, or high stringency conditions with (i) the mature polypeptide coding sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; (ii) the cDNA sequence contained in or the genomic DNA sequence comprising the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; or (iii) a full-length complementary strand of (i) or (ii);

(c) a polypeptide encoded by a polynucleotide comprising a nucleotide sequence having at least 60% identity, preferably at least 65%, 70%, 75%, 80%, 85%, 90%, 95%, 97%, or 98% identity to the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17;

(d) a polypeptide comprising one or more of the following motifs, preferably comprising two or more, three or more, four or more, five or six of the following motifs:

```
Motif I:    [FL]XX[YF]S[AN]X[FHY]G[GN]GX[YF]N    (SEQ ID NO: 40)

Motif II:   G[GN]GX[YF]NXX[VA]AX[EH][LF]R        (SEQ ID NO: 41)

Motif III:  RXXRI[QE][DEQ]S[IM]ATN               (SEQ ID NO: 42)

Motif IV:   S[IM]ATN[PG][EQN][FM][SDN][FL]       (SEQ ID NO: 43)

Motif V:    P[PDK][DG]F[HFW]R[AP]                (SEQ ID NO: 44)

Motif VI:   [TI]XXXLYPNP[TK][GV];                (SEQ ID NO: 45)
``` and (e) a variant comprising a substitution, deletion, and/or insertion of one or several amino acids of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19.

In a preferred embodiment, the polypeptide of the first aspect comprises or consists of the amino acid sequence of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19; or a fragment thereof having peroxygenase activity; preferably the polypeptide comprises or consists of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19.

A preferred embodiment relates to the the polypeptide of the first aspect, which is encoded by a polynucleotide that hybridizes under at least medium stringency conditions, preferably under at least medium-high stringency condition, more preferably under at least high stringency conditions, with (i) the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; (ii) the cDNA sequence contained in or the genomic DNA sequence comprising the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; or (iii) a full-length complementary strand of (i) or (ii).

Another preferred embodiment relates to the polypeptide of the first aspect, which is encoded by a polynucleotide comprising a nucleotide sequence having at least 60% identity, preferably at least 65%, 70%, 75%, 80%, 85%, 90%, 95%, 97%, or 98% identity to the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17.

It is also preferred that the polypeptide of the first aspect is encoded by a polynucleotide comprising or consisting of the nucleotide sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17; or a subsequence thereof encoding a fragment having peroxygenase activity; preferably the polypeptide is encoded by a polynucleotide comprising or consisting of the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17.

In another preferred embodiment of the invention, the polypeptide of the first aspect comprises one or more of the following motifs, preferably two or more, three or more, four or more, five or six of the following motifs:

```
Motif I:    [FL]XX[YF]S[AN]X[FHY]G[GN]GX[YF]N    (SEQ ID NO: 40)

Motif II:   G[GN]GX[YF]NXX[VA]AX[EH][LF]R        (SEQ ID NO: 41)

Motif III:  RXXRI[QE][DEQ]S[IM]ATN               (SEQ ID NO: 42)

Motif IV:   S[IM]ATN[PG][EQN][FM][SDN][FL]       (SEQ ID NO: 43)

Motif V:    P[PDK][DG]F[HFW]R[AP]                (SEQ ID NO: 44)

Motif VI:   [TI]XXXLYPNP[TK][GV]                 (SEQ ID NO: 45)
```

It is preferred that the the polypeptide of the first aspect is a variant comprising a substitution, deletion, and/or insertion of one or several amino acids of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., peroxygenase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14 or SEQ ID NO:19 is 10, preferably 9, more preferably 8, more preferably 7, more preferably at most 6, more preferably 5, more preferably 4, even more preferably 3, most preferably 2, and even most preferably 1.

It is preferable that the the polypeptide of the first aspect is encoded by the polynucleotide contained in the plasmid which is contained in *E. coli* NN049991 deposited 14 Mar. 2008 under the terms of the Budapest Treaty with the DSMZ under accession number DSM 21289; or which is encoded by the polynucleotide contained in the plasmid which is contained in *E. coli* NN049992 deposited 14 Mar. 2008 under the terms of the Budapest Treaty with the DSMZ under accession number DSM 21290.

Another preferred embodiment relates to the polypeptide of the first aspect of the invention, wherein the mature polypeptide is amino acids 1 to 330 of SEQ ID NO: 2.

It is also preferred in the first aspect of the invention that the mature polypeptide coding sequence is nucleotides 152 to 1141 of SEQ ID NO: 1.

Hybridization

The nucleotide sequences of SEQ ID NO: 1, SEQ ID NO: 3; SEQ ID NO:5, SEQ ID NO:7, SEQ ID NO:9, SEQ ID NO:11, SEQ ID NO:13, SEQ ID NO:15, or SEQ ID NO:17; or a subsequence thereof; as well as the amino acid sequence of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19; or a fragment thereof; may be used to design nucleic acid probes to identify and clone DNA encoding polypeptides having peroxygenase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having peroxygenase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3; SEQ ID NO:5, SEQ ID NO:7, SEQ ID NO:9, SEQ ID NO:11, SEQ ID NO:13, SEQ ID NO:15, or SEQ ID NO:17; the cDNA sequence contained in or the genomic DNA sequence comprising the mature polypeptide coding sequence of SEQ ID NO: 1, SEQ ID NO: 3; SEQ ID NO:5, SEQ ID NO:7, SEQ ID NO:9, SEQ ID NO:11, SEQ ID NO:13, SEQ ID NO:15 or SEQ ID NO:17; its full-length complementary strand; or a subsequence thereof; under very low to very high stringency conditions. Molecules to which the nucleic acid probe hybridizes under these conditions can be detected using, for example, X-ray film.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Sources of Polypeptides

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having peroxygenase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having peroxygenase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having peroxygenase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having peroxygenase activity.

In another preferred aspect, the polypeptide is a *Streptococcus equisimilis, Streptococcus pyogenes, Streptococcus uberis,* or *Streptococcus equi* subsp. *Zooepidemicus* polypeptide having peroxygenase activity.

In another preferred aspect, the polypeptide is a *Streptomyces achromogenes, Streptomyces avermitilis, Streptomyces coelicolor, Streptomyces griseus,* or *Streptomyces lividans* polypeptide having peroxygenase activity.

A polypeptide having peroxygenase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having peroxygenase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having peroxygenase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having peroxygenase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica,*

*Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having having peroxygenase activity.

In another preferred aspect, the polypeptide is from a Basidiomycete of the Bolbitiaceae (e.g. *Agrocybe* spp.) or Coprinaceae (e.g. *Coprinus* spp.) families.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having peroxygenase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having peroxygenase activity of the present invention.

In a preferred aspect, the nucleotide sequence comprises or consists of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17. In another more preferred aspect, the nucleotide sequence comprises or consists of the sequence contained in the plasmid which is contained in *E. coli* NN049991 deposited 14 Mar. 2008 under the terms of the Budapest Treaty with the DSMZ under accession number DSM 21289; or which is encoded by the polynucleotide contained in the plasmid which is contained in *E. coli* NN049992 deposited 14 Mar. 2008 under the terms of the Budapest Treaty with the DSMZ under accession number DSM 21290. In another preferred aspect, the nucleotide sequence comprises or consists of the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17. In another preferred aspect, the nucleotide sequence comprises or consists of nucleotides 152 to 1141 of SEQ ID NO: 1. In another more preferred aspect, the nucleotide sequence comprises or consists of the mature polypeptide coding sequence contained in the plasmid which is contained in *E. coli* NN049991 deposited 14 Mar. 2008 under the terms of the Budapest Treaty with the DSMZ under accession number DSM 21289; or which is encoded by the polynucleotide contained in the plasmid which is contained in *E. coli* NN049992 deposited 14 Mar. 2008 under the terms of the Budapest Treaty with the DSMZ under accession number DSM 21290.

The present invention also encompasses nucleotide sequences that encode polypeptides comprising or consisting of the amino acid sequence of SEQ ID NO: 2, SEQ ID NO: 4, SEQ ID NO:6, SEQ ID NO:8, SEQ ID NO: 10, SEQ ID NO:12, SEQ ID NO: 14 or SEQ ID NO:19, or the mature polypeptides thereof, which differ from SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, or the mature polypeptide coding sequences thereof, by virtue of the degeneracy of the genetic code. The present invention also relates to subsequences of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, that encode fragments of SEQ ID NO: 2, SEQ ID NO: 4, SEQ ID NO:6, SEQ ID NO:8, SEQ ID NO: 10, SEQ ID NO:12, SEQ ID NO: 14 or SEQ ID NO:19 that have peroxygenase activity.

The present invention also relates to mutant polynucleotides comprising or consisting of at least one mutation in the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, in which the mutant nucleotide sequence encodes the mature polypeptide of SEQ ID NO: 2, SEQ ID NO: 4, SEQ ID NO:6, SEQ ID NO:8, SEQ ID NO: 10, SEQ ID NO:12, SEQ ID NO: 14 or SEQ ID NO:19.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of Basidiomycete, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for peroxygenase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, (ii) the cDNA sequence contained in or the genomic DNA sequence comprising the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, (ii) the cDNA sequence contained in or the genomic DNA sequence comprising the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17, or (iii) a full-length complementary strand of (i) or (ii); and (b) isolating the hybridizing polynucleotide, which encodes a polypeptide having peroxygenase activity. In a preferred aspect, the complementary strand is the full-length complementary strand of the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alcaline protease (aprH) and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids −43 to −1 of SEQ ID NO: 2. In another preferred aspect, the signal peptide coding sequence comprises or consists of nucleotides 23 to 151 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but are not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but are not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17, wherein the mutant nucleotide sequence encodes a polypeptide that comprises or consists of the mature polypeptide of SEQ ID NO: 2, SEQ ID NO: 4, SEQ ID NO:6, SEQ ID NO:8, SEQ ID NO: 10, SEQ ID NO:12, SEQ ID NO: 14, or SEQ ID NO:19, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Transgenic Plants

The present invention also relates to plants, e.g., a transgenic plant, plant part, or plant cell, comprising an isolated polynucleotide encoding a polypeptide having peroxygenase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having peroxygenase activity of the present invention under conditions conducive for production of the polypeptide; and (b) recovering the polypeptide.

Removal or Reduction of Peroxygenase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of peroxygenase activity by fermentation of a cell that produces both a polypeptide of the present invention as well as the protein product of interest by adding an effective amount of an agent capable of inhibiting peroxygenase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of peroxygenase activity by cultivating the cell under conditions permitting the expression of the product, subjecting the resultant culture broth to a combined pH and temperature treatment so as to reduce the peroxygenase activity substantially, and recovering the product from the culture broth. Alternatively, the combined pH and temperature treatment may be performed on an enzyme preparation recovered from the culture broth. The combined pH and temperature treatment may optionally be used in combination with a treatment with a peroxygenase inhibitor.

In accordance with this aspect of the invention, it is possible to remove at least 60%, preferably at least 75%, more preferably at least 85%, still more preferably at least 95%, and most preferably at least 99% of the peroxygenase activity. Complete removal of peroxygenase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially peroxygenase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The peroxygenase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from peroxygenase activity that is produced by a method of the present invention.

Compositions

The present invention also relates to compositions comprising a polypeptide of the present invention. Preferably, the compositions are enriched in such a polypeptide. The term "enriched" indicates that the peroxygenase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art. The present invention is also directed to methods for using the polypeptides having peroxygenase activity, or compositions thereof.

Enzymatic Oxygenation of Aromatic N-Heterocycles to the Corresponding N-Oxides

The starting compounds of the formula (I) are preferably reacted with the aromatic haloperoxidase peroxygenase of the fungus *Agrocybe aegerita* (*Agrocybe aegerita* peroxygenase–*Agrocybe aegerita* peroxidase=AaP1), which has a particularly high peroxygenase activity, and at least one oxidizing agent, whereas the regioselective oxygenation of the heterocyclic nitrogen occurs.

The oxidizing agents used according to the invention are preferably $H_2O_2$, organic peroxides or hydroperoxides, for example tert-butyl hydroperoxide, air or oxygen (O$_2$). It is possible in the present process to dispense with expensive electron donors, for example NADH or NADPH (concentration of the oxidizing agent: 0.01 to 10 mmol/l, preferably 0.1 to 2 mmol/l, of H$_2$O$_2$).

To further accelerate the conversion of the compound of the formula (I) with the enzyme AaP1, it is additionally possible to add H$_2$O$_2$-generating enzymes, particularly oxidases, for example glucose oxidase or aryl alcohol oxidase and substrates thereof (glucose or benzyl alcohol), to the reaction mixture.

The basis of the enzymatic, cell-free process according to the invention is a novel extracellular haloperoxidase peroxygenase (=aromatic peroxygenase) which possesses P450-like catalysis properties and, in the presence of a suitable oxidizing agent (e.g. peroxides), particularly in buffered aqueous solutions, oxidizes aromatic N-heterocycles (e.g. pyridine) to the corresponding N-oxides, and in doing so achieves a high selectivity (>95% N-oxide).

The enzyme used is a specific extracellular heme-thiolate protein with peroxidase and peroxygenase function. It is formed by Basidiomycetes of the Bolbitiaceae (e.g. *Agrocybe* spp.) and Coprinaceae (e.g. *Coprinus* spp.) families and is characterized by specific catalytic properties which distinguish it clearly from peroxidases and cytochrome P450 enzymes described so far. The enzyme production is preferably carried out in liquid culture, in bioreactors and nitrogen-rich media (Ullrich, R., 2005, *Thesis*, IHI Zittau; Kluge, M. 2006, *Diploma thesis*, IHI Zittau).

The reactions catalysed by the enzyme known as AaP1, in contrast to chemical syntheses, do not require highly concentrated, aggressive and environmentally harmful reagents, and, when recovering the product, it is possible to dispense with chemical-intensive and time-consuming purification steps to separate the isomer mixtures. Typically, the enzyme is used in a concentration of 0.02 U/ml to 10 U/ml of AaP1, especially of 0.09 to 8 U/ml of AaP1. This makes the reaction process described particularly environmentally friendly.

A further advantage over purely chemical syntheses consists in the operation due to the inventive peroxygenase-catalysed reaction at room temperature and standard air pressure. In a preferred embodiment, the process is performed in aqueous, buffered solution. To stabilize the reaction in the aqueous medium, it is possible to add buffers based on organic acids, preferably citric acid, and phosphates, preferably potassium hydrogen-phosphate, to the reaction mixture (buffer concentration: 5 mmol/l to 500 mmol/l, preferably 20 to 100 mmol/l). Furthermore, it is possible to carry out the reaction in pH states without buffer with continuous metered addition of acids or bases.

To improve the solubility, organic solvents can be added to the reaction mixture and it is also possible to work in a two-phase system. Solvents usable according to the invention are protic solvents, such as methanol or ethanol, or aprotic polar solvents such as ethers (e.g. diisopropyl ether), acetone, acetonitrile, DMSO (dimethyl sulphoxide) and DMF (N,N-dimethylformamide).

The starting compounds of the formula (I) used are particularly compounds from the following group: pyridine, substituted pyridines (R=—X, —NO$_2$, -alkyl, -phenyl, —NH$_2$, —OH), quinoline, isoquinoline and derivatives thereof, aromatics with several heteroatoms and polycyclic N-heterocycles. The reaction is performed within a range of from 5° C. to 40° C., preferably at 20-30° C. The reaction times are typically in the range of from 0.5 to 120 minutes, particularly in the range of from 5 to 30 minutes. The yields of N-oxides achieved are within the range of from 10% to 99%, preferably between 20 and 90%. The advantages of the peroxygenase-catalysed reaction of N-heterocycles over catalysis with the only other enzyme capable of oxidizing pyridine to pyridine N-oxide (methane monooxygenase, MMO) consist of:

i) in the higher specific activity
ii) in the use of inexpensive peroxides instead of expensive electron donors [NAD(P)H],
iii) in the independence of the hydroxylating enzyme from flavin reductases and regulatory proteins,
iv) in the simple enzyme recovery without cell disruption and
v) in the high stability of the extracellular AaP1 and similar peroxygenases compared to the unstable intracellular and partly membrane-bound MMO.

With the AaP1-catalysed reactions, it is possible for the first time to convert nonactivated N-heterocycles such as pyridine with the aid of a single extracellular biocatalyst which requires only a peroxide as a cosubstrate in a one-stage process regioselectively to the corresponding N-oxides (e.g. pyridine N-oxide). The process can be used in a wide variety of different sectors of synthesis chemistry, inter alia for the preparation of active ingredients, pharmaceutical intermediates, specific catalysts and oxidizing agents, and for the introduction of protecting groups into unstable molecules. The invention will be illustrated in more detail below with reference to the example shown in the drawing, in which the invention is not restricted to the examples.

Applications of Peroxygenases in the Pulp & Paper Industry.

The peroxygenase can in a preferred embodiment be used for different applications within the pulp & paper industry. The enzyme can be used to increase delignification in bleaching processes of Kraft pulps, mechanical pulps and chemi-mechanical pulps. The aim in the bleaching processes is to remove the brown colored lignin molecules from the cellulose fibers; this is traditionally typically done in bleaching sequences using oxidative chemicals as chlorine dioxide, oxygen, ozone or hydrogen peroxide including as well alkaline extractions in between the oxidative steps.

By oxygenation of the aromatic structures in the lignin molecules the lignin will become more hydrophilic and will when further degraded by the traditional oxidative chemicals be easier to extract from the pulp, in that way less traditional bleaching chemicals are needed to obtain the same brightness level of the pulp. Also potential side chain hydroxylation of the aromatic structures, cleavage of alkyl-aryl ethers and oxidation of the alcohol and aldehyde structures which are present in the complex lignin structures will improve the bleaching process and save traditional chemicals.

In another embodiment also related to delignification of e.g. Kraft pulps the peroxygenase can be used for in situ generation of mediators to be used in laccase/mediator or peroxidase/mediator delignification a process described by e.g. Call et al, Journal of Biotechnology 53 (1997) p. 163-202. Mediator species of the so called N—OH type like e.g. hydroxybenzotriazole are compounds showing high delignification effects in this process. Hydroxybenzotriazole can be generated in situ in the process by hydroxylation of the much cheaper compound benzotriazole by the use of the peroxygenase. Other heterocyclic compounds of the N—OH type could be generated the same way.

In another embodiment the peroxygenase enzyme can be used to improve pitch removal/deresination of both chemical, mechanical and chemi-mechanical pulps. Pitch and resin are commonly used terms for the hydrophobic compounds found naturally in the wood. The resin is removed/degraded in the traditional chemical pulping processes to a certain extent but some of the compounds are difficult to remove to the desired extent due to the hydrophobicity of these compounds, hydroxylation of aromatic structures or oxidation of arylalcohol or phenolic structures can improve deresination and in that way improve pulp/paper properties, save downtime for cleaning and potentially save chemicals otherwise added to keep the hydrophobic compounds homogeneously suspended in the pulp.

Peroxygenase within the Water Treatment Industry

Peroxygenase can be applied for various purposes within the water treatment industry. Practically all of the envisioned applications correspond to peroxygenase catalyzed modification of recalcitrant, toxic persistent and/or bioactive substances. Modification (i.e. oxidation) of these substances will facilitate their mitigation by conventional water treatment operations including but not limited to activated sludges, bioreactors (e.g. moving bed, upflow sludge blanket, membrane, etc.), aerobic and anaerobic digesters, clarifiers and lagoons.

The claimed benefits of specific and catalytic activity of the peroxygenases within water treatment operations can be grouped according to the primary deliverable of the modification.

In the first scenario, peroxygenase-mediated modification of the substance reduces the hazardous nature of the substance directly and/or by increasing the bioavailability of the hazardous substance for subsequent removal by conventional water treatment operations. Examples include persistent substances such as herbicides/fungicides (e.g. phenyl urea, phenoxy), atrazine, phenylhydrocarbons & PAH, insecticides, DDT, PCB, PCDD, PCDF and surfactants as well as emerging micropollutants (EMPs) such as endocrine disruptors, pharmaceuticals (e.g. antibiotics/anti-bacterial agents, estrogenic hormones), personal care products and the like. For the most part, the substances tend to be present at low concentration levels which makes the selectivity and specificity of peroxygenases preferred over more expensive treatments that tend to be unselective, non-catalytic and non-regenerative.

In the second scenario, peroxygenase modification of substances improves the efficacy/performance of the water treatment operations. Oxidation of recalcitrant organics (i.e. "non-treated" and "non-treatable/inert/hard COD") by the peroxygenase lowers the COD:BOD ratio which may increase the overall removal rate of conventional water treatment operations without major capital investment. In a similar fashion, the peroxygenase-mediated oxidation of potentially toxic substances may improve the health and efficacy of biological nutrient removal (BNR) systems (e.g. reactors, digesters, lagoons, sludges, beds, filters and clarifiers). In addition to improved organic removal rates, the peroxygenase may enhance methanogenesis by detoxification of influent and lowering of the COD:BOD ratio.

In a third scenario, peroxygenase activity may be used to reduce residual peroxides present in industrial effluents with the concomitant oxidation of local substances.

In a fourth scenario, peroxygenase activity may be used to improve the flocculating behaviour of primary and secondary/biological sludges. By catalyzing the formation of covalent bridges between colloids and colloids and between colloids and larger flocs, the amount of chemical used to condition the sludge before conventional dewatering (e.g. thickener, press, bed, centrifuge, plate and frame, etc.) may be reduced and/or the dewatering behaviour of the sludge may be improved with or without added chemistries.

Peroxygenase Applications within Enzymatic Oil Treatment

Petroleum products are the most important source of energy and raw materials; however, as the worlds oil reserves become scarce heavy crude oil and bituminous deposits will have to be utilized alongside the various developments in renewable energy sources. Heavy crude oil is highly viscous and hard to extract: In addition heavy crude oil contains high amount of sulfur, nitrogen, aromatics and heavy metals; compounds which must be reduced prior to utilization. Different potential applications for utilizing biotechnology, in particular oxidoreductase based technology, in refining of petroleum are mentioned by Ayala, M. et al. (Biocatalysis and Biotransformation, 2007, 25:2, 114-129. The different embodiments are further described below:

Asphaltenes are defined as the part of petroleum that is insoluble in N-alkanes but soluble in toluene. The asphaltene fraction is thought to be largely responsible for undesirable oil properties like high viscosity and the propensity to form emulsions, polymers and coke. Nitrogen, oxygen and sulfur heteroatoms are present as non- and heterocyclic groups. In addition, a significant amount of porphyrins (petroporphyrins) can be found containing nickel and vanadium. Modification of asphaltenes using peroxygenase will have a range of beneficial effects: Increased water solubility, increased boiling point, lower intermolecular interactions, lower viscosity and improved biological reactivity. Hence, peroxygenases can be applied prior to upgrading resulting in lower viscosity and reducing the need for solvents and formation of coke. Combined or subsequent reaction with oxidoreductases, in particular laccase, phenoloxidase, haloperoxidase, and peroxidase, or microorganisms, in particular *Rhodococcus erythropolis* or similar bacterial cells, will further enhance the modification or degradation. The treatment can be conducted prior to desalting, in combination with desalting or during or following subsequent processing like vacuum distillation, hydrotreater, hydrocracker or fluid catalytic cracker. Two phase systems in water or water miscible solvents can optionally be applied.

Presence of aromatic compounds in refined fuels leads to incomplete combustion and a concomitant formation of particulate matter. Polycyclic aromatic hydrocarbons are considered a potential health risk because of their carcinogenic and mutagenic activity. Treatment of polycyclic aromatic hydrocarbons with peroxygenase results in products which are more soluble and significantly less mutagenic than the parent compound.

Heavy metal ions like vanadium and nickel are naturally present in Canadian Oil Sands bitumen on the order of 300 ppm or higher. These ions are known to be held tightly via chelation with biomarkers called petroporphyrins within bitumen. Metal ions are deleterious to the upgrading of bitumen in that they act to poison the downstream catalysts used during cracking and hydrotreating. Heavy metals in petroleum lead to two other major problems. One is the formation of ash with high concentration of metal oxides, resulting in waste disposal issues. Second is poisoning of the catalysts during catalytic cracking decreasing the selectivity and activity. Currently, there is no remedy for alleviating these problems; the current practice is to utilize large volumes of catalyst.

There has been research into using biotechnology within the refining industry, although commercial applications are not yet known. It was shown in the early 1990's by Fedorak et al that a heme-peroxidase enzyme called chloroperoxidase (CPO) from *C. fumago* was capable of breaking the chelation of metal ions by oxidative ring-opening of petroporphyrin. The released metal ion was subsequently extracted from the organic layer into the water layer, away from the bitumen. In the late 1990's, Torres and Vazquez-Duhalt showed similar reactivity using cytochrome c (a small heme protein with peroxidase-like activity).

Although these enzymes showed interesting activity against petroporphyrins, they have several drawbacks that will make them impossible for use for large-scale industrial applications. First of all, in the presence of their substrate (eg: hydrogen peroxide), the enzymes themselves get oxidized and lose activity. The heme active site is known to get oxidized by $H_2O_2$; the half-lives of these enzymes are on the order of minutes in 1 mM $H_2O_2$. Secondly, enzyme expression levels are very low.

Treatment of oil, bitumen, asphaltenes or petroporphyrins with peroxygenase significantly reduces the content of heavy metals, especially the content of nickel and vanadium. The treatment is preferable conducted at any stage prior to the catalytic cracker.

Regulations regarding liquid hydrocarbon fuels are continuously requiring lower sulfur content. Traditionally desulfurization is performed during hydrotreating, where in addition nitrogen, oxygen and arsenic compounds are reduces or removed. Peroxygenase treatment can significantly reduce the sulfur content, in particular if followed by a distillation step. The treatment can be conducted prior to desalting, in combination with desalting or during or following subsequent processing like vacuum distillation, hydrotreater, hydrocracker or fluid catalytic cracker.

Applications of Fungal Peroxygenase in Drug/Chemical Synthesis

Similar to cytochrom P450 enzymes the peroxygenases may be used in the chemical synthesis of various chemicals, including active pharmaceutical ingredients and intermediates, and specifically the peroxygenases may be advantageously used for the synthesis of optically pure chiral compounds. Examples of such possible peroxygenase catalysed reactions are:

11 beta-hydroxylation of Reichstein S to hydrocortisone (U.S. Pat. No. 4,353,985)

Conversion of Progesterone into Cortisone (steroid modification/production).

Production of Pravastin, an anti-cholesterol drug, from compactin (Biotechnol. Lett. 2003, 25, 1827).

Hydroxylation of R-2-phenoxy propionic acid at the 4-position.

Biocatalytic production of anticancer drug perillyl alcohol from limone using a P450 enzyme (Appl. Environ. Microbiol. 2005, 71, 1737).

Of particular relevance are compounds that contain N-oxidized forms of pyridine, pyrrole, pyrrollidine, piperidine, imidazole, thiazole, morpholine or pyrimidine (Source Refs: J. B. van Beilen, et al., *Trends Biotechnol.*, 2003, 21, 170. and V. B. Urlacher and S. Eiben, *Trends Biotechnol.*, 2006, 24, 324).

Peroxygenase Application in Detergent Compositions

The peroxygenase enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274—make references to specific sequences and positions.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444—make references to specific sequences and positions.

Commercially available amylases are Duramyl™, Termamyl™, Fungamyl™ and BAN™ (Novozymes A/S), Rapidase™ and Purastar™ (from Genencor International Inc.).
Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).
Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202 which is hereby incorporated as reference.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1

Cloning of Peroxygenase Genes from *A. Aegerita* and *C. Radians*

Culture conditions, activity measurement, and purification of enzyme were previously described for *Agrocybe aegerita* peroxidase (Ullrich et al., 2004, Appl. Env. Microbiol. 70(8): 4575-4581) and for *Coprinus radians* peroxidase (Anh et al., 2007, Appl Env Microbiol 73(17): 5477-5485).
Isolation of Nucleic Acids and cDNA Synthesis Mycelium of *Coprinus radians* (strain DSMZ 888, cultivation day 12) and *Agrocybe aegerita* (strain TM-A1-K, cultivation day 16) was obtained by filtration from shaking cultures (particular growth conditions described above). After subsequent lyophilisation (Alpha 2-4 freeze-dryer, Christ, Osterode, Germany) genomic DNA was isolated using a protocol previously described (Nikolcheva and Bärlocher, 2002). Trizol reagent (Invitrogen, Karlsruhe, Germany) was used to isolate total RNA, which was stored at −80° C.

For cDNA synthesis, total RNA (1.0 microgram) was primed by using a polyT-anchor primer (polyT-anchor2-primer in case of *Coprinus radians*). Afterwards, the total mRNA was reverse transcribed to cDNA with the anchor sequence added to the 3' end by using a "RevertAid™ H Minus M-MuLV" reverse transcriptase (Fermentas, St. Leon-Rot, Germany); furthermore by adding 1 microliter TS-Short-primer (10 micromolar) to the reaction mix an anchor sequence was added to the 5' end of the cDNA using a protocol according to Matz et al. (1999).
PCR Conditions For PCR (polymerase chain reaction) amplifications a "MasterCycler EP Gradient S" gradient cycler (Eppendorf, Hamburg, Germany) was applied. All primers were obtained from MWG Biotech (Ebersberg, Germany). Primers used for cDNA synthesis, 3' RACE (rapid amplification of cDNA ends) and 5' RACE experiments are listed in table 1. Degenerate primers are listed in table 2. Specific primers for AaP genes are listed in table 3. Nested PCRs were performed with the 1:100 diluted PCR products.

TABLE 1

Primer for cDNA synthesis, 3' and 5' RACE. Primer sequences are written according to IUPAC nucleotide codes, the letters 'rg' represent ribonucleotide guanosine.

| Primer name | Primer sequence (5' → 3') | SEQ ID NO: |
|---|---|---|
| polyT-anchor-primer | tagctcgatgcttgcacgcttttttttttttttttt | 20 |
| AP-primer | tagctcgatgcttgcacgc | 21 |
| polyT-anchor2-primer | tgtaaccgcgtatcagtgcttttttttttttttttttv | 22 |
| AP2-primer | tgtaaccgcgtatcagtgc | 23 |
| TS-short-primer | aagcagtggtatcaacgcagagtacgcrgrgrg | 24 |
| heel-carrier primer | gtaatacgactcactatagggcaagcagtggtatcaacgcagagt | 25 |
| heel-specific primer | gtaatacgactcactatagggc | 26 |

TABLE 2

Degenerate primers written according to IUPAC nucleotide codes, letter 'i' represents inosine wobble base.

| Primer name | Primer sequence (5' → 3') | SEQ ID NO: |
|---|---|---|
| Cop1-For | cciccnccigartaygt | 27 |
| Cop5-For | gaycayaaratgcc | 28 |
| Cop6-Rev | ccaraartcrtcnggcat | 29 |
| Aap1-For | garcciggnaarcciccignnc | 30 |
| Aap2-Rev | gciarngtrttiariccngg | 31 |
| Aap4-For | aaygciacnaayccng | 32 |
| Aap4-Rev | aartciggrttngtngc | 33 |
| Aap6-Rev | ariccngtiggrttngg | 34 |

TABLE 3

Specific primers for AaP genes. Primer names are underlined to distinguish between degenerate and specific AaP primers

| Primer name | Primer sequence (5' 3') | SEQ ID NO: |
|---|---|---|
| <u>1Aap-For1</u> | cgcaacatgaaatacttcagc | 35 |
| <u>1Aap-For2</u> | gagccaacacaacctcctggac | 36 |
| <u>1Aap-Rev4</u> | ggcataaggtcactggagtcc | 37 |
| <u>2Aap-For1</u> | ttctacatgaaatattttcc | 38 |
| <u>2Aap-Rev2</u> | aagcaggttgttggaccg | 39 |

The PCR reactions (25 microliter) contained 10 microliter PCR Master Mix (HotMaster Mix™, 2.5-fold concentrated; 5Prime, Hamburg, Germany), 1 microliter of each primer from 10 micromolar stock solutions in case of specific primers and from 100 micromolar stock solutions for degenerated primers, 1 microliter of cDNA and PCR grade water. The PCR started with an initial denaturation at 95° C. for 3 min, followed by 35 cycles of denaturation at 95° C. for 45 s, annealing at 52.7° C. (in case of degenerated primers) or temperature according to "4+2 rule" (Rychlik and Rhoads (1989), in case of specific primers) for 45 s and elongation at 72° C. for 1.5 min. Final elongation took 10 min at 72° C.

The resulting PCR products were purified (SureClean™, Bioline, Luckenwalde, Germany) and cloned.

Cloning, Sequencing, and Sequence Analysis

Plasmids derived from dU/A-cloning of PCR fragments with the pSTBlue-1 AccepTor™ Vector Kit (Merck (Novagen), Darmstadt, Germany) were verified by colony PCR (Sambrook and Maniatis, 1989) and several independent clones were used for sequencing.

Sequencing was performed on ALFexpressII equipment in combination with AutoRead Sequencing™ Kit (both GE Healthcare, Munich, Germany). Software BioEdit 7.0 was used for sequence analyses and multiple alignments (Hall, 1999, Nucleic Acids Symp Ser 41, 95-98).

*Coprinus radians*: Based on the knowledge of the peptide sequence of the N-terminus and one internal peptide fragment degenerated primers were used on cDNA to partially amplify a fragment of a haloperoxidase gene in *Coprinus radians* (strain DMSZ 888). The initial PCR product which was derived from application of the degenerated primers Cop1-For and Cop6-Rev (size of approximately 700 bp) was purified, cloned, one clone was sequenced (SEQ ID NO:15), and identified as homologue to CPO sequence by a basic local alignment search tool (BLAST) search. In order to obtain the 3' end of the cDNA, a rapid amplification of cDNA ends (3' RACE) was performed. The AP2-primer was used in combination with the degenerated primer Cop5-For to amplify a fragment (approximately 500 bp) from the cDNA, which was cloned and completely sequenced afterwards (SEQ ID NO:17) (three independent clones).

*Agrocybe aegerita*: Based on the knowledge of the peptide sequence of the N-terminus and 5 internal peptide fragments degenerate primers were used on cDNA to amplify fragments of a haloperoxidase gene in *Agrocybe aegerita* (strain TM-A1-K). One initial PCR product which were derived from application of degenerate primers Aap1-For and Aap6-Rev (size of approximately 880 bp). Two 3' RACE-PCR products were generated by using PCR with AaP1-For and AP primer (approximately 1200 bp) and by using PCR with AaP4-For and AP primer (nested PCR, approximately 650 bp), respectively. All three fragments were purified from agarose gel, purified and cloned. Several independent clones were fully sequenced; all sequences were assembled to a synthetic sequence.

The synthetic sequence was identified as homologous to CPO sequence by a basic local alignment search tool (BLAST) search. A 5' RACE were performed with specific primer mix SO-Mix (contain 90% heel-specific primer and 10% heel-carrier primer, 10 micromolar) and degenerate primer AaP4-Rev. The diluted PCR product were then used in a nested PCR with SO-Mix and degenerate primer AaP2-Rev. The resulting band with approx. 350 bp were excised from gel, purified and cloned. Several independent clones were fully sequenced.

Two different, but homologous sequences were discovered. One sequence overlapped with the already known synthetic sequence and completed the cDNA sequence of AaP1 gene. Based on this data specific primers were designed for both the AaP1 gene and AaP2 gene.

Performing PCR at cDNA level with primer combination 1AaP-For1 and 1AaP-Rev4 resulted in a complete full-length cDNA sequence fragment of AaP1 gene. This fragment was cloned and one clone was completely sequenced (SEQ ID NO:1). This clone was deposited on 14 Mar. 2008 at DSMZ as *Escherichia coli* NN049991 with accession number DSM 21289.

For completion of the AaP2 gene at cDNA level a 3' RACE was performed: A PCR with primer combination 2AaP-For1 and AP primer resulted in an about 1300 bp long fragment. This fragment was also cloned, two clones were fully sequenced and revealed the whole cDNA sequence of AaP2 gene (SEQ ID NO:2). This clone was deposited on 14 Mar. 2008 at DSMZ as *Escherichia coli* NN049992 with accession number DSM 21290.

After completion of cDNA sequences specific primers were used in PCRs to amplify genomic fragments of AaP genes. The primer combination 1AaP-For2 and 1AaP-Rev4 was used to amplify the gene region of AaP1 from genomic DNA (about 1400 bp), which encodes the mature protein without the signal peptide and comprises the whole 3'UTR, too. The primer combination 2AaP-For1 and 2AaP-Rev2 was used to amplify the complete CDS and 3'UTR of AaP2 gene from genomic DNA (about 1500 bp). Both PCR products were purified, clone and at least two independent clones were fully sequenced.

Example 2

Amino Acid Motifs Characteristic of Fungal Peroxygenases

We analyzed the full-length peroxygenase amino acid sequences of AaP1 and AaP2 and found that they are unique in that the mature peptide sequence can be viewed as comprising two domains.

The first half of the AaP1 amino acid sequence (SEQ ID NO:2) aligns convincingly well with chloroperoxidase, CPO. The second, c terminal half of the AaP1 peptide does not share homology with any amino acid sequences in the databases, aside from *Laccaria* and *Coprinus cinereus* putative open reading frame sequences identified through genome-sequencing.

It is highly probable that the two domain structure in which the N terminal half shares similarity to known chloroperoxidases while the C terminal portion does not, is a clear characteristic of this class of peroxygenases.

We have aligned the amino-acid sequences deduced herein with a number of similar sequences in FIGS. 4A-D and have identified some identifying conserved motifs. Patterns for motif searching are based on the format of pattern used in the PROSITE database, with the difference that the terminating dot '.' and the hyphens, '-', between the characters are optional. The PROSITE pattern definition from the PROSITE documentation follows:

The standard IUPAC one-letter codes for the amino acids are used.

The symbol 'x' is used for a position where any amino acid is accepted.

Ambiguities are indicated by listing the acceptable amino acids for a given position, between square parentheses '[ ]'. For example: [ALT] stands for Ala or Leu or Thr.

Ambiguities are also indicated by listing between a pair of curly brackets '{ }' the amino acids that are not accepted at a given position. For example: {AM} stands for any amino acid except Ala and Met.

Each element in a pattern is separated from its neighbor by a '-'. (Optional in patmatdb and fuzzpro).

Repetition of an element of the pattern can be indicated by following that element with a numerical value or a numerical range between parenthesis. Examples: x(3) corresponds to x-x-x, x(2,4) corresponds to x-x or x-x-x or x-x-x-x.

When a pattern is restricted to either the N- or C-terminal of a sequence, that pattern either starts with a '<' symbol or respectively ends with a '>' symbol.

A period ends the pattern. (Optional in patmatdb and fuzzpro).

In order to exclude classic chloroperoxidases, we limited our search for conserved motifs to the C-terminal half of the aligned peroxygenase proteins. We identified the following conserved motifs as very useful for finding peroxygenases:

Such motifs or profiles can be entered into a search program, such as Fuzzpro, for the identification of novel fungal peroxygenases (Fuzzpro was written by Alan Bleasby, European Bioinformatics Institute, Wellcome Trust Genome Campus, Hinxton, Cambridge CB10 1SD, UK). Fuzzpro is part of the EMBOSS package (EMBOSS: The European Molecular Biology Open Software Suite (2000), Rice, P. Longden, I. and Bleasby, A. Trends in Genetics 16, (6) pp 276-277).

The percent identity matrix shown in table 4 was calculated based on "all against all" alignments of the peroxygenase amino acid sequences listed in the sequence listing. The entry in row i and column j in the matrix is calculated as the number of exact matches in the alignment between sequence i and sequence j divided by the total length of the alignment minus the total length of the gaps in the alignment. Each alignment is done using the Needle program from the EMBOSS package (www.emboss.org) version 2.8.0. The program Needle implements the global alignment algorithm described in Needleman, S. B. and Wunsch, C. D. (J. Mol. Biol., 1970, 48: 443-453); and Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley. The alignments used the following parameters:

Gap opening penalty: 10.00
Gap extension penalty: 0.50
Substitution matrix: BLOSUM62

TABLE 4

Symmetrical %-identity matrix of the peroxygenase amino acid sequences listed in the sequence listing.

| | | | | | | | | |
|---|---|---|---|---|---|---|---|---|
| SEQ ID NO: 2 | 100 | 73.58 | 61.89 | 58.18 | 54.20 | 60.43 | 59.88 | 58.88 |
| SEQ ID NO: 4 | | 100 | 62.23 | 59.30 | 58.43 | 61.41 | 62.05 | 62.46 |
| SEQ ID NO: 6 | | | 100 | 60.05 | 57.39 | 59.40 | 59.21 | 62.89 |
| SEQ ID NO: 8 | | | | 100 | 62.14 | 58.89 | 58.81 | 60.99 |
| SEQ ID NO: 10 | | | | | 100 | 56.77 | 57.84 | 63.45 |
| SEQ ID NO: 12 | | | | | | 100 | 82.40 | 58.82 |
| SEQ ID NO: 14 | | | | | | | 100 | 57.89 |
| SEQ ID NO: 19 | | | | | | | | 100 |

Example 3

Construction of *Aspergillus* Recombinant Expression Hosts

The cDNA sequences encoding the entire open reading frames of AaP1 and AaP2 are listed in SEQ ID NO's:1 and 3, respectively. PCR primers were designed to amplify the entire open reading frames from the ATG start codon until the termination codon. The primers were synthesized with 15 base pair 5' sequences homologous to the border of the cloning site for HindIII-BamHI cut pDau109 *Aspergillus* expression vector. pDau109 is disclosed in WO 2005042735, which is incorporated herein by reference. Thus the primers con-

```
Motif I:     [FL]XX[YF]S[AN]X[FHY]G[GN]GX[YF]N    (SEQ ID NO: 40)

Motif II:    G[GN]GX[YF]NXX[VA]AX[EH][LF]R        (SEQ ID NO: 41)

Motif III:   RXXRI[QE][DEQ]S[IM]ATN               (SEQ ID NO: 42)

Motif IV:    S[IM]ATN[PG][EQN][FM][SDN][FL]       (SEQ ID NO: 43)

Motif V:     P[PDK][DG]F[HFW]R[AP]                (SEQ ID NO: 44)

Motif VI:    [TI]XXXLYPNP[TK][GV]                 (SEQ ID NO: 45)
``` sisted of two regions, one region specific to the peroxygenase and with an approximate annealing temperature of 50 degrees or over, and the 15 base pairs homologous to the expression plasmid at the restriction enzyme borders.

Plasmid pDau109 was double digested with BamHI and HindIII and the vector was purified from the stuffer fragment by agarose gel electrophoresis and use of Illustra™ DNA and gel band purification kit (GE Healthcare). The primers are shown below:

```
Primer AaP1F:
                                        (SEQ ID NO: 46)
5' acacaactggggatccaccatgaaatacttcagcctgttc Primer AaP1R:
                                        (SEQ ID NO: 47)
5' agatctcgagaagcttaatctcgcccgtacgggaat Primer AaP2F:
                                        (SEQ ID NO: 48)
5' acacaactggggatccaccatgaaatattttcccctgttcc Primer AaP2R:
                                        (SEQ ID NO: 49)
5' agatctcgagaagcttaatctcgcccgtatgggaag
```

The underlined portions of the primers are designed to overlap with the cloning site in the vector and are needed for InFusion™ cloning later.

The PCR reactions used to generate the expression cassettes were performed as follows:

The Phusion Hot Start™ high fidelity DNA polymerase (F-540, New England Biolabs) system was used to amplify the expression cassettes from the cDNA plasmids. The buffer for GC rich templates was used instead of the standard buffer. An MJ Research PTC-200 DNA engine was used to perform the PCR reaction. The following conditions were used:
GC 5× buffer 10 microliter
20 mM dNTP 1 microliter
Primer F 1 microliter
Primer R 1 microliter
DNA template 10 ng 1 microliter
dH2O 35.5 microliter
Phusion Hot (2 u/ul) 0.5 microliter
PCR Program:
95° C. for 30 sec
25 cycles of:
98° C. for 10 sec
50° C. for 20 sec
72° C. for 30 sec
Final extension at 72° C. for 10 minutes The reaction was cooled to 10° C. after the PCR program ended. 25 microliter of each PCR product were run on a 1% agarose TBE gel and the single PCR band was purified using Illustra DNA and gel band purification kit (GE Healthcare). The purified PCR product was then ready for cloning. The InFusion™ system for cloning was used for cloning the fragments into the prepared vector (BD Biosciences). The cloning protocol was followed exactly as described in the InFusion™ instruction manual. The treated plasmid and insert were transformed into InFusion™ Blue *E. coli* cells according to the protocol and plated on LB with 50 mg/liter ampicillin.

After incubating at 37° C. overnight, colonies were seen growing under selection on the LB ampicillin plates. 10 colonies of the AaP1 construct and 10 colonies of the AaP2 construct were cultivated in LB liquid with 50 mg/ml ampicillin and plasmid was isolated according to the JETQUICK™ Plasmid Purification Spin Kit procedure (Genomed).

Isolated plasmids were sequenced with vector primers in order to determine a representative plasmid expression clone that was free of PCR errors. One error free AaP1 clone and one error free AaP2 clone were selected for further work:
NP003506: Aap1 peroxygenase
NP003507: Aap2 peroxygenase Plasmid DNA is then isolated using the JETSTAR 2.0 Plasmid Mini/Midi/Maxi-Protocol (Genomed). Thus purified plasmid DNA is transformed into a standard fungal expression host, such as *Aspergillus oryzae*, according to the method of WO 2005/042735, pages 34-35, which are incorporated herein by reference. *Aspergillus* transformants able to produce a recombinant AaP protein as judged by SDS PAGE analysis are then fermented in either small (200 ml) or very large (over 15 m$^3$ tanks) to produce enough culture fluid for subsequent filtration, concentration and/or purification of the recombinant produced enzyme(s).

Example 4

Cloning of *Laccaria bicolor* Peroxygenase

A suitable expression cassette is obtained from either genomic *L. bicolor* DNA (SEQ ID NO:5) or cDNA therefrom using primers designed, for example, for InFusion™ cloning, as described in the previous section. A suitable primer set amplifying the entire open reading frame and suitable for expression in pDau109 is as follows:

```
Forward primer:
                                        (SEQ ID NO: 50)
5' acacaactggggatccaccatggctcgccttactttcct Reverse primer:
                                        (SEQ ID NO: 51)
5' agatctcgagaagcttactttccataagggaagatctg
```

The underlined sequences represent vector sequence needed for the InFusion™ cloning procedure described in detail above. The resulting 1167 bp fragment will have 15 bp overlaps with BamHI-HindIII cut pDau109 vector.

Recombinant expression in, e.g., *Aspergillus oryzae* is done as described in the above for the AaP1 and AaP2 enzymes.

Example 5

Cloning of *Coprinus cinereus* Peroxygenases

A suitable expression cassette is obtained from either genomic *Coprinus cinereus* DNA or cDNA (SEQ ID NO's: 7, 9, 11, 13, or 15) therefrom using primers designed, for example, for InFusion™ cloning, as described in the previous section. A suitable primer set amplifying the entire open reading frame of one of the peroxygenases (SEQ ID NO:8) and suitable for expression in pDau109 is as follows:

```
Forward primer:
                                        (SEQ ID NO: 52)
5' acacaactggggatccaccatgatctcgacctcgaagca Reverse primer:
                                        (SEQ ID NO: 53)
5' agatctcgagaagcttaatcactcttgccccaggg
```

The underlined sequences represent vector sequence needed for the InFusion™ cloning procedure described in detail above. The resulting fragment will have 15 bp overlaps with BamHI-HindIII cut pDau109 vector.

A suitable primer set amplifying the entire open reading frame of one of the peroxygenases (SEQ ID NO:10) and suitable for expression in pDau109 is as follows:

```
Forward primer:
                                       (SEQ ID NO: 54)
5' acacaactggggatccaccatggtttcgtgcaagctcc Reverse primer:
                                       (SEQ ID NO: 55)
5' agatctcgagaagcttacagtgtaccatacggtttca
```

The underlined sequences represent vector sequence needed for the InFusion™ cloning procedure described in detail above. The resulting fragment will have 15 bp overlaps with BamHI-HindIII cut pDau109 vector.

A suitable primer set amplifying the entire open reading frame of one of the peroxygenases (SEQ ID NO:12) and suitable for expression in pDau109 is as follows:

```
Forward primer:
                                       (SEQ ID NO: 56)
5' acacaactggggatccaccatgaacggtctgttcgcca Reverse primer:
                                       (SEQ ID NO: 57)
5' agatctcgagaagcttagttacgtccgtaggggaac
```

The underlined sequences represent vector sequence needed for the InFusion™ cloning procedure described in detail above. The resulting fragment will have 15 bp overlaps with BamHI-HindIII cut pDau109 vector.

A suitable primer set amplifying the entire open reading frame of one of the peroxygenases (SEQ ID NO:14) and suitable for expression in pDau109 is as follows:

```
Forward primer:
                                       (SEQ ID NO: 58)
5' acacaactggggatccaccatgctcaaaccgcgtgttc Reverse primer:
                                       (SEQ ID NO: 59)
5' agatctcgagaagcttaatcgtgtccgtaagggaaaa
```

The underlined sequences represent vector sequence needed for the InFusion™ cloning procedure described in detail above. The resulting fragment will have 15 bp overlaps with BamHI-HindIII cut pDau109 vector.

Recombinant expression in, e.g., *Aspergillus oryzae* of each of the *Coprinus* peroxygenases listed above is done as described in the previous section for the AaP1 and AaP2 enzymes.

Example 6

Conversion of Pyridine to Pyridine N-Oxide by AaP1 Enzyme 2 mM pyridine is dissolved in aqueous potassium phosphate buffer solution (20 mM, pH=7.0) and stirred in a closed glass vessel at 24° C. together with 2 mM $H_2O_2$ (20×100 micromolar) and 2 U of *Agrocybe aegerita* AaP1 peroxidase (units based on the oxidation of veratryl alcohol to veratrylaldehyde; Ullrich et al., 2004, Appl. Environ. Microbiol: 70, 4575-81) in a total volume of 1 ml. The reaction time was a total of 120 min (quenching of the reaction with 25 mM NaOH).

The product detected from this reaction (yield 25%) was exclusively pyridine N-oxide with reference to an authentic standard (Fluka) via the retention time and UV and mass spectrum. The chromatographic separation and product identification were effected using a specific column (Phenomex synergi 4 microns Fusion-RP 80A, 150×2 mm) and an Agilent LC-MS-DAD system.

The invention claimed is:

1. An isolated polypeptide having peroxygenase activity, selected from the group consisting of:
   (a) a polypeptide comprising an amino acid sequence having at least 90% identity to the polypeptide of SEQ ID NO: 8; and
   (b) a polypeptide encoded by a polynucleotide comprising a nucleotide sequence having at least 90% identity to the mature polypeptide coding sequence of SEQ ID NO:7.

2. The isolated polypeptide of claim 1, wherein the polypeptide comprises an amino acid sequence having at least 90% identity to the polypeptide of SEQ ID NO: 8.

3. The isolated polypeptide of claim 1, wherein the polypeptide comprises an amino acid sequence having at least 95% identity to the polypeptide of SEQ ID NO: 8.

4. The isolated polypeptide of claim 1, wherein the polypeptide comprises an amino acid sequence having at least 97% identity to the polypeptide of SEQ ID NO: 8.

5. The isolated polypeptide of claim 1, wherein the polypeptide comprises an amino acid sequence having at least 98% identity to the polypeptide of SEQ ID NO: 8.

6. The isolated polypeptide of claim 1, wherein the polypeptide is encoded by a polynucleotide comprising a nucleotide sequence having at least 90% identity to the mature polypeptide coding sequence of SEQ ID NO:7.

7. The isolated polypeptide of claim 1, wherein the polypeptide consists of an amino acid sequence having the amino acid sequence of SEQ ID NO: 8.

8. The isolated polypeptide of claim 1, wherein the polypeptide encoded by the polynucleotide of SEQ ID NO:7.

9. A nucleic acid construct comprising the polynucleotide of claim 1 operably linked to one or several control sequences that direct the production of the polypeptide in an expression host.

10. An isolated recombinant host cell comprising the nucleic acid construct of claim 9.

11. A method of producing the polypeptide of claim 1, comprising: (a) cultivating an isolated cell, which in its wild-type form produces the polypeptide of claim 1, under conditions conducive for production of the polypeptide; and (b) recovering the polypeptide.

12. A method of producing the polypeptide of claim 1, comprising: (a) cultivating an isolated host cell comprising a nucleic acid construct comprising a nucleotide sequence encoding the polypeptide of claim 1 under conditions conducive for production of the polypeptide; and (b) recovering the polypeptide.

13. A process for enzymatic, regioselective oxygenation of N-heterocycles of the formula (I) in FIG. 1 to corresponding N-oxides of the formula (II) in FIG. 1, by converting N-heterocycles of the formula (I) in FIG. 1 with a peroxygenase polypeptide as defined in claim 1 in the presence of at least one oxidizing agent in a one-stage reaction process.

14. The process of claim 13, characterized in that the N-heterocycle used is pyridine.

15. The process of claim 13, wherein further $H_2O_2$-generating enzymes are added to the reaction mixture to further accelerate the reaction of the compound of the formula (I) with the peroxygenase polypeptide.

* * * * *

SEQUENCE LISTING

```
<160> NUMBER OF SEQ ID NOS: 59

<210> SEQ ID NO 1
<211> LENGTH: 1273
<212> TYPE: DNA
<213> ORGANISM: Agrocybe aegerita
<220> FEATURE:
<221> NAME/KEY: CDS
<222> LOCATION: (23)..(1141)
<220> FEATURE:
<221> NAME/KEY: sig_peptide
<222> LOCATION: (23)..(151)
<220> FEATURE:
<221> NAME/KEY: mat_peptide
<222> LOCATION: (152)..(1141)
<220> FEATURE:
<221> NAME/KEY: misc_feature
<222> LOCATION: (152)..(590)
<223> OTHER INFORMATION: chloroperoxidase similar region
<220> FEATURE:
<221> NAME/KEY: misc_feature
<222> LOCATION: (594)..(1141)
<223> OTHER INFORMATION: novel fungal peroxygenase specific region

<400> SEQUENCE: 1
ggtcacaaca ccccagcgca ac atg aaa tac ttc agc ctg ttc ccg acc ttg      52
                         Met Lys Tyr Phe Ser Leu Phe Pro Thr Leu
                         -40                        -35
```

-continued

| | | |
|---|---|---|
| ata ttt gca gcg ggg gtc atc gca ttt ccc tca cat gct tca ttg gcc<br>Ile Phe Ala Ala Gly Val Ile Ala Phe Pro Ser His Ala Ser Leu Ala<br>          -30                       -25                       -20 | 100 | |
| ggc ctc agc gag cag gaa ctg gat gag atc att cct aca ctc gaa att<br>Gly Leu Ser Glu Gln Glu Leu Asp Glu Ile Ile Pro Thr Leu Glu Ile<br>          -15                       -10                       -5 | 148 | |
| cga gag cca aca caa cct cct gga cct ccg gag gac acc tct gcc aaa<br>Arg Glu Pro Thr Gln Pro Pro Gly Pro Pro Glu Asp Thr Ser Ala Lys<br>-1  1                    5                      10                    15 | 196 | |
| ttg gtg aat gac aag gat cac cca tgg aag cca ctt cga ccg ggc gac<br>Leu Val Asn Asp Lys Asp His Pro Trp Lys Pro Leu Arg Pro Gly Asp<br>           20                      25                       30 | 244 | |
| atc cgt ggg cct tgt ccc ggt ctc aac acg ttg gcg tct cat ggg tac<br>Ile Arg Gly Pro Cys Pro Gly Leu Asn Thr Leu Ala Ser His Gly Tyr<br>         35                        40                       45 | 292 | |
| ctc ccg aga aac ggg gtt gca act ccg gcg caa att atc aac gct gtc<br>Leu Pro Arg Asn Gly Val Ala Thr Pro Ala Gln Ile Ile Asn Ala Val<br>         50                        55                       60 | 340 | |
| cag gaa gga ttc aac atg gat aat tca gtc gca ctc ttt gcg acg tat<br>Gln Glu Gly Phe Asn Met Asp Asn Ser Val Ala Leu Phe Ala Thr Tyr<br>         65                        70                       75 | 388 | |
| gag gca cac ctt atg gtc ggc aat ctc ctc acg gac ttg ctg agt atc<br>Glu Ala His Leu Met Val Gly Asn Leu Leu Thr Asp Leu Leu Ser Ile<br>80                  85                       90                       95 | 436 | |
| gga cgc aag acg ccg ctc act ggg cct gat ctc cca ccc cca gct aac<br>Gly Arg Lys Thr Pro Leu Thr Gly Pro Asp Leu Pro Pro Pro Ala Asn<br>                100                       105                     110 | 484 | |
| att ggt ggg ctc agt gag cat ggg ctc ttt gaa ggt gat gct agt atg<br>Ile Gly Gly Leu Ser Glu His Gly Leu Phe Glu Gly Asp Ala Ser Met<br>                115                       120                     125 | 532 | |
| act aga ggt gac gca ttc ttc ggc aac aat gat gag ttc aat gaa gaa<br>Thr Arg Gly Asp Ala Phe Phe Gly Asn Asn Asp Glu Phe Asn Glu Glu<br>                130                       135                     140 | 580 | |
| ctc ttc caa cag ttc att gac tac agt aac cga ttc gga gga ggg tac<br>Leu Phe Gln Gln Phe Ile Asp Tyr Ser Asn Arg Phe Gly Gly Gly Tyr<br>     145                       150                     155 | 628 | |
| tac aac ctt acg gtg gca gtg gaa ctc cgc ttc aag cgt att cag gac<br>Tyr Asn Leu Thr Val Ala Val Glu Leu Arg Phe Lys Arg Ile Gln Asp<br>160                 165                       170                     175 | 676 | |
| tcg att gcg acc aac ccc gaa ttt aac ttt gtc tcc ccg aga ttc ttt<br>Ser Ile Ala Thr Asn Pro Glu Phe Asn Phe Val Ser Pro Arg Phe Phe<br>                180                       185                     190 | 724 | |
| gct gcc tac ggc gaa tct gtc gcc ccc aat aac ttt ttc gtc gat gga<br>Ala Ala Tyr Gly Glu Ser Val Ala Pro Asn Asn Phe Phe Val Asp Gly<br>                195                       200                     205 | 772 | |
| cgc aag gac gac ggg cat ttg gat atg gac gcc gcc cgt gga ttt ttc<br>Arg Lys Asp Asp Gly His Leu Asp Met Asp Ala Ala Arg Gly Phe Phe<br>          210                       215                     220 | 820 | |
| caa ttc ggc cgc atg cct gac ggc ttc ttc cgc cca aac gga acg aaa<br>Gln Phe Gly Arg Met Pro Asp Gly Phe Phe Arg Pro Asn Gly Thr Lys<br>     225                       230                     235 | 868 | |
| ggc aac gca gga ctc gat gac gtc gta cgg gct cat ccc gta cag cct<br>Gly Asn Ala Gly Leu Asp Asp Val Val Arg Ala His Pro Val Gln Pro<br>240                 245                       250                     255 | 916 | |
| gga agg aat ctc ggc cga gtc aac agc tac act cat gat cca aca tcc<br>Gly Arg Asn Leu Gly Arg Val Asn Ser Tyr Thr His Asp Pro Thr Ser<br>                260                       265                     270 | 964 | |
| gcc gat ttc acc act cct tgc tta ttg tac gag aac ttc gca aac aaa<br>Ala Asp Phe Thr Thr Pro Cys Leu Leu Tyr Glu Asn Phe Ala Asn Lys<br>     275                       280                     285 | 1012 | |

-continued

| | | | | | | | | | | |
|---|---|---|---|---|---|---|---|---|---|---|
| acc | gtc | acg | gca | ctc | tac | ccg | aat | ccg | aag | gga | caa | ctc | cgc | aga | gca | 1060 |
| Thr | Val | Thr | Ala | Leu | Tyr | Pro | Asn | Pro | Lys | Gly | Gln | Leu | Arg | Arg | Ala | |
| | | 290 | | | | 295 | | | | 300 | | | | | | |

| att | aaa | gcg | aat | ctc | cat | ttc | ctc | ttc | ctg | gca | ata | aac | aga | acc | gtc | 1108 |
| Ile | Lys | Ala | Asn | Leu | His | Phe | Leu | Phe | Leu | Ala | Ile | Asn | Arg | Thr | Val | |
| | 305 | | | | | 310 | | | | | 315 | | | | | |

| gga | tgc | gcc | gag | gta | ttc | ccg | tac | ggg | cga | gat | tgatgaggcg | ccacatgaga | 1161 |
| Gly | Cys | Ala | Glu | Val | Phe | Pro | Tyr | Gly | Arg | Asp | | | |
| 320 | | | | | 325 | | | | | 330 | | | | aagagtcggg cagtagtagt ccacttctt cgtaacagtt tgtagatgtc cgcgtattta 1221 aatatggact ccagtgacct tatgccgctt caaaaaaaaa aaaaaaaaaa aa 1273

<210> SEQ ID NO 2
<211> LENGTH: 373
<212> TYPE: PRT
<213> ORGANISM: Agrocybe aegerita

<400> SEQUENCE: 2

Met Lys Tyr Phe Ser Leu Phe Pro Thr Leu Ile Phe Ala Ala Gly Val
          -40                     -35                     -30

Ile Ala Phe Pro Ser His Ala Ser Leu Ala Gly Leu Ser Glu Gln Glu
          -25                     -20                     -15

Leu Asp Glu Ile Ile Pro Thr Leu Glu Ile Arg Glu Pro Thr Gln Pro
          -10                     -5           -1  1                 5

Pro Gly Pro Pro Glu Asp Thr Ser Ala Lys Leu Val Asn Asp Lys Asp
                        10                      15                      20

His Pro Trp Lys Pro Leu Arg Pro Gly Asp Ile Arg Gly Pro Cys Pro
                25                      30                      35

Gly Leu Asn Thr Leu Ala Ser His Gly Tyr Leu Pro Arg Asn Gly Val
         40                      45                      50

Ala Thr Pro Ala Gln Ile Ile Asn Ala Val Gln Glu Gly Phe Asn Met
         55                      60                      65

Asp Asn Ser Val Ala Leu Phe Ala Thr Tyr Glu Ala His Leu Met Val
70                      75                      80                      85

Gly Asn Leu Leu Thr Asp Leu Leu Ser Ile Gly Arg Lys Thr Pro Leu
                90                      95                      100

Thr Gly Pro Asp Leu Pro Pro Ala Asn Ile Gly Gly Leu Ser Glu
                105                     110                     115

His Gly Leu Phe Glu Gly Asp Ala Ser Met Thr Arg Gly Asp Ala Phe
        120                     125                     130

Phe Gly Asn Asn Asp Glu Phe Asn Glu Glu Leu Phe Gln Gln Phe Ile
        135                     140                     145

Asp Tyr Ser Asn Arg Phe Gly Gly Gly Tyr Tyr Asn Leu Thr Val Ala
150                     155                     160                     165

Val Glu Leu Arg Phe Lys Arg Ile Gln Asp Ser Ile Ala Thr Asn Pro
                170                     175                     180

Glu Phe Asn Phe Val Ser Pro Arg Phe Phe Ala Ala Tyr Gly Glu Ser
                185                     190                     195

Val Ala Pro Asn Asn Phe Val Asp Gly Arg Lys Asp Asp Gly His
        200                     205                     210

Leu Asp Met Asp Ala Ala Arg Gly Phe Phe Gln Phe Gly Arg Met Pro
        215                     220                     225

Asp Gly Phe Phe Arg Pro Asn Gly Thr Lys Gly Asn Ala Gly Leu Asp
230                     235                     240                     245

Asp Val Val Arg Ala His Pro Val Gln Pro Gly Arg Asn Leu Gly Arg
                250                     255                     260

```
Val Asn Ser Tyr Thr His Asp Pro Thr Ser Ala Asp Phe Thr Thr Pro
            265                 270                 275

Cys Leu Leu Tyr Glu Asn Phe Ala Asn Lys Thr Val Thr Ala Leu Tyr
            280                 285                 290

Pro Asn Pro Lys Gly Gln Leu Arg Arg Ala Ile Lys Ala Asn Leu His
295                 300                 305

Phe Leu Phe Leu Ala Ile Asn Arg Thr Val Gly Cys Ala Glu Val Phe
310                 315                 320                 325

Pro Tyr Gly Arg Asp
            330

<210> SEQ ID NO 3
<211> LENGTH: 1284
<212> TYPE: DNA
<213> ORGANISM: Agrocybe aegerita
<220> FEATURE:
<221> NAME/KEY: CDS
<222> LOCATION: (25)..(1137)

<400> SEQUENCE: 3
ggtcagaaca cagcacggtt ctac atg aaa tat ttt ccc ctg ttc cca acc       51
                          Met Lys Tyr Phe Pro Leu Phe Pro Thr
                            1               5 ttg gtc ttc gca gcg agg gtc gtt gct ttt cct gcc tac gcc tca ttg      99
Leu Val Phe Ala Ala Arg Val Val Ala Phe Pro Ala Tyr Ala Ser Leu
 10              15                  20                  25 gcc ggc ctc agc cag cag gaa ttg gac gct ata atc cca aca ctc gag     147
Ala Gly Leu Ser Gln Gln Glu Leu Asp Ala Ile Ile Pro Thr Leu Glu
                 30                  35                  40 gcc cga gag cca gga tta cct cct ggt cct ctc gag aat agc tct gca     195
Ala Arg Glu Pro Gly Leu Pro Pro Gly Pro Leu Glu Asn Ser Ser Ala
             45                  50                  55 aag ttg gtg aac gac gag gct cac cca tgg aag ccg ctt cga cct ggc     243
Lys Leu Val Asn Asp Glu Ala His Pro Trp Lys Pro Leu Arg Pro Gly
         60                  65                  70 gat att cgt gga cct tgc cct ggt ctc aat act ctg gca tct cac ggg     291
Asp Ile Arg Gly Pro Cys Pro Gly Leu Asn Thr Leu Ala Ser His Gly
     75                  80                  85 tac ctc ccg aga aat ggc gtt gca acc ccg gtg caa ata ata aac gcg     339
Tyr Leu Pro Arg Asn Gly Val Ala Thr Pro Val Gln Ile Ile Asn Ala
 90                  95                 100                 105 gtt cag gaa gga ctc aat ttc gac aat caa gcc gca gtc ttc gcc aca     387
Val Gln Glu Gly Leu Asn Phe Asp Asn Gln Ala Ala Val Phe Ala Thr
                110                 115                 120 tat gcg gcc cac ctt gtg gac ggc aat ctc att acg gac ttg ctg agc     435
Tyr Ala Ala His Leu Val Asp Gly Asn Leu Ile Thr Asp Leu Leu Ser
            125                 130                 135 atc gga cgc aag acg cgg ctc act ggg cct gat cca cca ccc ccc gct     483
Ile Gly Arg Lys Thr Arg Leu Thr Gly Pro Asp Pro Pro Pro Pro Ala
        140                 145                 150 tcc gtt ggt gga ctc aat gag cat ggc acc ttc gaa ggc gac gcc agt     531
Ser Val Gly Gly Leu Asn Glu His Gly Thr Phe Glu Gly Asp Ala Ser
    155                 160                 165 atg acc cga ggt gac gca ttc ttt ggc aac aac cac gat ttc aat gag     579
Met Thr Arg Gly Asp Ala Phe Phe Gly Asn Asn His Asp Phe Asn Glu
170                 175                 180                 185 acg ctc ttc gaa cag ttg gtt gac tac agc aac cga ttt gga gga gga     627
Thr Leu Phe Glu Gln Leu Val Asp Tyr Ser Asn Arg Phe Gly Gly Gly
                190                 195                 200 aaa tac aat ctt acc gtc gcg ggg gag ctc cgt ttc aag cgc att caa     675
```

```
                    Lys Tyr Asn Leu Thr Val Ala Gly Glu Leu Arg Phe Lys Arg Ile Gln
                                    205                 210                 215 gac tcc att gcg acc aac ccc aat ttc tcc ttt gtt gac ttt agg ttc                723
Asp Ser Ile Ala Thr Asn Pro Asn Phe Ser Phe Val Asp Phe Arg Phe
220                 225                 230 ttt act gct tac ggc gag acc acc ttc ccc gcg aat ctt ttt gtg gat                771
Phe Thr Ala Tyr Gly Glu Thr Thr Phe Pro Ala Asn Leu Phe Val Asp
        235                 240                 245 ggg cgc agg gac gac ggc cag cta gat atg gat gct gca cgg agt ttt                819
Gly Arg Arg Asp Asp Gly Gln Leu Asp Met Asp Ala Ala Arg Ser Phe
250                 255                 260                 265 ttc caa ttc agc cgt atg cct gac gat ttc ttc cgc gca ccc agc ccg                867
Phe Gln Phe Ser Arg Met Pro Asp Asp Phe Phe Arg Ala Pro Ser Pro
                270                 275                 280 aga agt ggc aca gga gtc gag gta gtt ata cag gct cat cct atg cag                915
Arg Ser Gly Thr Gly Val Glu Val Val Ile Gln Ala His Pro Met Gln
            285                 290                 295 ccc gga aga aat gtc ggc aag atc aac agc tac acc gtc gac cca aca                963
Pro Gly Arg Asn Val Gly Lys Ile Asn Ser Tyr Thr Val Asp Pro Thr
        300                 305                 310 tcc tct gac ttt tcc acc ccc tgc ttg atg tac gag aaa ttc gtc aac                1011
Ser Ser Asp Phe Ser Thr Pro Cys Leu Met Tyr Glu Lys Phe Val Asn
315                 320                 325 ata acg gtc aag tca ctc tac ccg aat ccg acg gtg cac gtt cgc aaa                1059
Ile Thr Val Lys Ser Leu Tyr Pro Asn Pro Thr Val His Val Arg Lys
330                 335                 340                 345 gcc ctt aat acg aat ctc gat ttc ttc ttc cag gga gtc gcc gct gga                1107
Ala Leu Asn Thr Asn Leu Asp Phe Phe Phe Gln Gly Val Ala Ala Gly
                350                 355                 360 tgt acc cag gtc ttc cca tac ggg cga gat tgatatgata gagacaagag                  1157
Cys Thr Gln Val Phe Pro Tyr Gly Arg Asp
            365                 370 agagtgtttc gacagtagcg gttctcaatt tgaatagttt gcagacatct gcttgtgtaa             1217
atacactctt gcggtccaac aacctgcttt tctctggcca ccttcaaaaa aaaaaaaaaa             1277
aaaaaaa                                                                        1284

<210> SEQ ID NO 4
<211> LENGTH: 371
<212> TYPE: PRT
<213> ORGANISM: Agrocybe aegerita

<400> SEQUENCE: 4

Met Lys Tyr Phe Pro Leu Phe Pro Thr Leu Val Phe Ala Ala Arg Val
1               5                   10                  15

Val Ala Phe Pro Ala Tyr Ala Ser Leu Ala Gly Leu Ser Gln Gln Glu
            20                  25                  30

Leu Asp Ala Ile Ile Pro Thr Leu Glu Ala Arg Glu Pro Gly Leu Pro
        35                  40                  45

Pro Gly Pro Leu Glu Asn Ser Ser Ala Lys Leu Val Asn Asp Glu Ala
    50                  55                  60

His Pro Trp Lys Pro Leu Arg Pro Gly Asp Ile Arg Gly Pro Cys Pro
65                  70                  75                  80

Gly Leu Asn Thr Leu Ala Ser His Gly Tyr Leu Pro Arg Asn Gly Val
                85                  90                  95

Ala Thr Pro Val Gln Ile Ile Asn Ala Val Gln Glu Gly Leu Asn Phe
            100                 105                 110

Asp Asn Gln Ala Ala Val Phe Ala Thr Tyr Ala Ala His Leu Val Asp
        115                 120                 125
```

Gly Asn Leu Ile Thr Asp Leu Leu Ser Ile Gly Arg Lys Thr Arg Leu
            130                 135                 140

Thr Gly Pro Asp Pro Pro Pro Ala Ser Val Gly Leu Asn Glu
145                 150                 155                 160

His Gly Thr Phe Glu Gly Asp Ala Ser Met Thr Arg Gly Asp Ala Phe
                165                 170                 175

Phe Gly Asn Asn His Asp Phe Asn Glu Thr Leu Phe Glu Gln Leu Val
            180                 185                 190

Asp Tyr Ser Asn Arg Phe Gly Gly Lys Tyr Asn Leu Thr Val Ala
            195                 200                 205

Gly Glu Leu Arg Phe Lys Arg Ile Gln Asp Ser Ile Ala Thr Asn Pro
210                 215                 220

Asn Phe Ser Phe Val Asp Phe Arg Phe Phe Thr Ala Tyr Gly Glu Thr
225                 230                 235                 240

Thr Phe Pro Ala Asn Leu Phe Val Asp Gly Arg Arg Asp Asp Gly Gln
                245                 250                 255

Leu Asp Met Asp Ala Ala Arg Ser Phe Phe Gln Phe Ser Arg Met Pro
            260                 265                 270

Asp Asp Phe Phe Arg Ala Pro Ser Pro Arg Ser Gly Thr Gly Val Glu
            275                 280                 285

Val Val Ile Gln Ala His Pro Met Gln Pro Gly Arg Asn Val Gly Lys
290                 295                 300

Ile Asn Ser Tyr Thr Val Asp Pro Thr Ser Ser Asp Phe Ser Thr Pro
305                 310                 315                 320

Cys Leu Met Tyr Glu Lys Phe Val Asn Ile Thr Val Lys Ser Leu Tyr
                325                 330                 335

Pro Asn Pro Thr Val His Val Arg Lys Ala Leu Asn Thr Asn Leu Asp
            340                 345                 350

Phe Phe Phe Gln Gly Val Ala Ala Gly Cys Thr Gln Val Phe Pro Tyr
            355                 360                 365

Gly Arg Asp
    370

```
<210> SEQ ID NO 5
<211> LENGTH: 1947
<212> TYPE: DNA
<213> ORGANISM: Laccaria bicolor
<220> FEATURE:
<221> NAME/KEY: exon
<222> LOCATION: (547)..(822)
<220> FEATURE:
<221> NAME/KEY: CDS
<222> LOCATION: (547)..(822)
<220> FEATURE:
<221> NAME/KEY: sig_peptide
<222> LOCATION: (547)..(610)
<220> FEATURE:
<221> NAME/KEY: Intron
<222> LOCATION: (823)..(885)
<220> FEATURE:
<221> NAME/KEY: exon
<222> LOCATION: (886)..(943)
<220> FEATURE:
<221> NAME/KEY: CDS
<222> LOCATION: (886)..(943)
<220> FEATURE:
<221> NAME/KEY: Intron
<222> LOCATION: (944)..(991)
<220> FEATURE:
<221> NAME/KEY: exon
<222> LOCATION: (992)..(1162)
<220> FEATURE:
<221> NAME/KEY: CDS
```

<222> LOCATION: (992)..(1162)
<220> FEATURE:
<221> NAME/KEY: Intron
<222> LOCATION: (1163)..(1218)
<220> FEATURE:
<221> NAME/KEY: exon
<222> LOCATION: (1219)..(1239)
<220> FEATURE:
<221> NAME/KEY: CDS
<222> LOCATION: (1219)..(1239)
<220> FEATURE:
<221> NAME/KEY: Intron
<222> LOCATION: (1240)..(1288)
<220> FEATURE:
<221> NAME/KEY: exon
<222> LOCATION: (1289)..(1341)
<220> FEATURE:
<221> NAME/KEY: CDS
<222> LOCATION: (1289)..(1341)
<220> FEATURE:
<221> NAME/KEY: Intron
<222> LOCATION: (1342)..(1392)
<220> FEATURE:
<221> NAME/KEY: exon
<222> LOCATION: (1393)..(1944)
<220> FEATURE:
<221> NAME/KEY: CDS
<222> LOCATION: (1393)..(1944)

<400> SEQUENCE: 5

```
agacaaagtt ttttgatcga ctggccttct gatctacaga aatctccgct gtgtccggtt      60
aggatatcta ttcgaagata tctcctttca ttgctgagta atttgctgcg tcggtcaggc     120
ttcagcttca taccataccc aagaacgtgt ctcgcccatt tacaggtgat ctggaggtga     180
ggtttataaa tagaacggac tataagcgga ctaaccttgg acgttatata gtgcaaacct     240
ggtacaagct cacggttcac cctcgggttt taaaaattat gacccgaaag gtcaactgca     300
ttttatatct cctgcgtgtt aacttcgctt gtaagtcgtc gacgctatga aaaaactacg     360
gatcgagtca ttgacgggct ggcaagtttc ctgccactgc ggaagctgaa agcaccgcat     420
cgccttttaa agtcgatgtg accttagccc agctgcccct ggtcattcac agcattctga     480
gatcattgtc acgagtataa ataggtgtg tgtaggcgtc gaattccaac aattcagtcg      540
```

| | | | | | |
|---|---|---|---|---|---|
| tgcata atg gct cgc ctt act ttc ctc gca gct att gcc ctg gca tta | | | | | | 588 |
| Met Ala Arg Leu Thr Phe Leu Ala Ala Ile Ala Leu Ala Leu | | | | | | |
| 1               5                   10 | | | | | | |

```
tct tcc acc act gta cta gca ttc cca tca tac ggc tcc ctt gct ggg       636
Ser Ser Thr Thr Val Leu Ala Phe Pro Ser Tyr Gly Ser Leu Ala Gly
 15                  20                  25                  30 ctt tca gag gcg gaa tta gac cgt att att ccc ttg cta gaa gct cgt       684
Leu Ser Glu Ala Glu Leu Asp Arg Ile Ile Pro Leu Leu Glu Ala Arg
                 35                  40                  45 aac gct ggc cct cct cct gga cca ctg aag aat act tca aca aaa ttg       732
Asn Ala Gly Pro Pro Pro Gly Pro Leu Lys Asn Thr Ser Thr Lys Leu
             50                  55                  60 gtc aac gac aag aac cac ccc tgg aag cct ctc gga tat ggc gat att       780
Val Asn Asp Lys Asn His Pro Trp Lys Pro Leu Gly Tyr Gly Asp Ile
 65                  70                  75 cga ggt cct tgc cct ggg tta aac aca ctg gcc tcc cat ggg                822
Arg Gly Pro Cys Pro Gly Leu Asn Thr Leu Ala Ser His Gly
                 80                  85                  90 gtgagttcgg acatttatgg ttacgtttca tcggagttaa ttgtaactgt tttattcgtg     882 cag tgg ctt cct cga aac ggc atc gct act ccg gcg caa att gtc aac       930
    Trp Leu Pro Arg Asn Gly Ile Ala Thr Pro Ala Gln Ile Val Asn
             95                  100                 105 gcg gtg cag gaa g gtctgctgtt cgactaattg ctgacaattg atattgattg        983
Ala Val Gln Glu
```

```
                                                                            -continued Ala Val Gln Glu
        110 ttgcttag ga  ttc aat atg gga aat gat ttg gcg gtc ttc gtc aca tac            1032
             Gly Phe Asn Met Gly Asn Asp Leu Ala Val Phe Val Thr Tyr
                         115                 120                 125 gct gcg cat ctc gtt gac ggc aat cag gtc acg gac ttg ctt agc atc             1080
Ala Ala His Leu Val Asp Gly Asn Gln Val Thr Asp Leu Leu Ser Ile
            130                 135                 140 ggt gga aag acg cct caa aca ggc cct gac ccg ccc gcg cct gcc att             1128
Gly Gly Lys Thr Pro Gln Thr Gly Pro Asp Pro Pro Ala Pro Ala Ile
        145                 150                 155 gtc ggt ggt ctc aat acg cac gcc gta ttt gaa g gtatgtaatc                    1172
Val Gly Gly Leu Asn Thr His Ala Val Phe Glu
160                 165 acgatttgtc gactctggag accttctgac atctatttga ttgaag gt  gat gca              1226
                                                      Gly Asp Ala
                                                              170 agt atg act cga g gtatgatcat cgccccgata attagatgac aattgaaccg               1279
Ser Met Thr Arg
        175 agcccttag ga  gac gca ttt ttc gga gat aac cac agc ttt aac gaa aca           1329
              Gly Asp Ala Phe Phe Gly Asp Asn His Ser Phe Asn Glu Thr
                                  180                 185 cag ttt gat gaa gtgagatatt tctacgcttg cagtcagtga aagattaatt                 1381
Gln Phe Asp Glu
190 tctcctcaca g ttt tct gcc ttc agc aac aaa ttc ggc ggg gga tac tac            1431
             Phe Ser Ala Phe Ser Asn Lys Phe Gly Gly Gly Tyr Tyr
                         195                 200                 205 aat ttg agc gta gca gcc gag ttt aga tgg cag cgc att caa gaa tct             1479
Asn Leu Ser Val Ala Ala Glu Phe Arg Trp Gln Arg Ile Gln Glu Ser
            210                 215                 220 att gcg acg aac cca aac ttt tct ctc atc tcc ccc cgt tac ttc acg             1527
Ile Ala Thr Asn Pro Asn Phe Ser Leu Ile Ser Pro Arg Tyr Phe Thr
        225                 230                 235 gcg tat gcc gag tcc gtg ttt ccc ctg gta ttc ttc gtc gac ggc cgc             1575
Ala Tyr Ala Glu Ser Val Phe Pro Leu Val Phe Phe Val Asp Gly Arg
240                 245                 250 gta tca gac gga cgg ctt agc cta ccg aac gcg cgt ggg ttc ttc cag             1623
Val Ser Asp Gly Arg Leu Ser Leu Pro Asn Ala Arg Gly Phe Phe Gln
255                 260                 265                 270 aat agc caa atg ccc aaa gac ttc ttc cgg ccc aat cag tct atc ggc             1671
Asn Ser Gln Met Pro Lys Asp Phe Phe Arg Pro Asn Gln Ser Ile Gly
            275                 280                 285 ctc aac gaa att ggt gat ggg att agc gct att gct agt gcc cac cct             1719
Leu Asn Glu Ile Gly Asp Gly Ile Ser Ala Ile Ala Ser Ala His Pro
        290                 295                 300 att gcg ccg gga aag aac gag gga gtt ggg aac tat gtc ctc gac cct             1767
Ile Ala Pro Gly Lys Asn Glu Gly Val Gly Asn Tyr Val Leu Asp Pro
305                 310                 315 aca tct gcg gat ttc gac cat ttc tgc ttg ctt tac atc aac ttc gtc             1815
Thr Ser Ala Asp Phe Asp His Phe Cys Leu Leu Tyr Ile Asn Phe Val
320                 325                 330 aac cag acc gta aag tca ctc tac ccc aat ccc aaa ggc gtt ttg ctc             1863
Asn Gln Thr Val Lys Ser Leu Tyr Pro Asn Pro Lys Gly Val Leu Leu
335                 340                 345                 350 gat gcc ttg aag agg aat ctc aac aat ttc tac ggc cca ctc aac ggg             1911
Asp Ala Leu Lys Arg Asn Leu Asn Asn Phe Tyr Gly Pro Leu Asn Gly
            355                 360                 365 tcg gat tgt gag cag atc ttc cct tat gga aag tag                             1947
```

```
Ser Asp Cys Glu Gln Ile Phe Pro Tyr Gly Lys
            370                 375

<210> SEQ ID NO 6
<211> LENGTH: 377
<212> TYPE: PRT
<213> ORGANISM: Laccaria bicolor

<400> SEQUENCE: 6

Met Ala Arg Leu Thr Phe Leu Ala Ala Ile Ala Leu Ala Leu Ser Ser
1               5                   10                  15

Thr Thr Val Leu Ala Phe Pro Ser Tyr Gly Ser Leu Ala Gly Leu Ser
            20                  25                  30

Glu Ala Glu Leu Asp Arg Ile Ile Pro Leu Leu Glu Ala Arg Asn Ala
        35                  40                  45

Gly Pro Pro Gly Pro Leu Lys Asn Thr Ser Thr Lys Leu Val Asn
    50                  55                  60

Asp Lys Asn His Pro Trp Lys Pro Leu Gly Tyr Gly Asp Ile Arg Gly
65                  70                  75                  80

Pro Cys Pro Gly Leu Asn Thr Leu Ala Ser His Gly Trp Leu Pro Arg
                85                  90                  95

Asn Gly Ile Ala Thr Pro Ala Gln Ile Val Asn Ala Val Gln Glu Gly
            100                 105                 110

Phe Asn Met Gly Asn Asp Leu Ala Val Phe Val Thr Tyr Ala Ala His
        115                 120                 125

Leu Val Asp Gly Asn Gln Val Thr Asp Leu Leu Ser Ile Gly Gly Lys
130                 135                 140

Thr Pro Gln Thr Gly Pro Asp Pro Ala Pro Ala Ile Val Gly Gly
145                 150                 155                 160

Leu Asn Thr His Ala Val Phe Glu Gly Asp Ala Ser Met Thr Arg Gly
                165                 170                 175

Asp Ala Phe Phe Gly Asp Asn His Ser Phe Asn Glu Thr Gln Phe Asp
            180                 185                 190

Glu Phe Ser Ala Phe Ser Asn Lys Phe Gly Gly Gly Tyr Tyr Asn Leu
        195                 200                 205

Ser Val Ala Ala Glu Phe Arg Trp Gln Arg Ile Gln Glu Ser Ile Ala
210                 215                 220

Thr Asn Pro Asn Phe Ser Leu Ile Ser Pro Arg Tyr Phe Thr Ala Tyr
225                 230                 235                 240

Ala Glu Ser Val Phe Pro Leu Val Phe Val Asp Gly Arg Val Ser
                245                 250                 255

Asp Gly Arg Leu Ser Leu Pro Asn Ala Arg Gly Phe Phe Gln Asn Ser
            260                 265                 270

Gln Met Pro Lys Asp Phe Phe Arg Pro Asn Gln Ser Ile Gly Leu Asn
        275                 280                 285

Glu Ile Gly Asp Gly Ile Ser Ala Ile Ala Ser Ala His Pro Ile Ala
    290                 295                 300

Pro Gly Lys Asn Glu Gly Val Gly Asn Tyr Val Leu Asp Pro Thr Ser
305                 310                 315                 320

Ala Asp Phe Asp His Phe Cys Leu Leu Tyr Ile Asn Phe Val Asn Gln
                325                 330                 335

Thr Val Lys Ser Leu Tyr Pro Asn Pro Lys Gly Val Leu Leu Asp Ala
            340                 345                 350

Leu Lys Arg Asn Leu Asn Asn Phe Tyr Gly Pro Leu Asn Gly Ser Asp
        355                 360                 365
```

```
Cys Glu Gln Ile Phe Pro Tyr Gly Lys
    370                 375
```

<210> SEQ ID NO 7
<211> LENGTH: 1164
<212> TYPE: DNA
<213> ORGANISM: Coprinopsis cinerea okayama7#130
<220> FEATURE:
<221> NAME/KEY: CDS
<222> LOCATION: (1)..(1161)

<400> SEQUENCE: 7

```
atg atc tcg acc tcg aag cat ctc ttt gtg ctt ctt cct ctt ttc cta     48
Met Ile Ser Thr Ser Lys His Leu Phe Val Leu Leu Pro Leu Phe Leu
1               5                   10                  15 gtc tca cat ctc tcc ctc gtt ctc ggt ttc ccg gcg tac gcg tcc ctt     96
Val Ser His Leu Ser Leu Val Leu Gly Phe Pro Ala Tyr Ala Ser Leu
            20                  25                  30 gga ggt tta acc gag cgt caa gtc gaa gag tac acg tcc aag ctc cct    144
Gly Gly Leu Thr Glu Arg Gln Val Glu Glu Tyr Thr Ser Lys Leu Pro
        35                  40                  45 atc gtc ttt cca cca ccg ccg cct gaa cct atc aag gac ccg tgg ctc    192
Ile Val Phe Pro Pro Pro Pro Pro Glu Pro Ile Lys Asp Pro Trp Leu
    50                  55                  60 aag ttg gtc aat gac agg gct cat cca tgg aga ccc ctt cgg aga gga    240
Lys Leu Val Asn Asp Arg Ala His Pro Trp Arg Pro Leu Arg Arg Gly
65                  70                  75                  80 gat gtc aga gga ccc tgc ccg ggg ttg aat acg ttg gca tcc cat ggg    288
Asp Val Arg Gly Pro Cys Pro Gly Leu Asn Thr Leu Ala Ser His Gly
                85                  90                  95 tat ctt cct cga gat ggt gtg gcg act cca gct caa atc atc act gcc    336
Tyr Leu Pro Arg Asp Gly Val Ala Thr Pro Ala Gln Ile Ile Thr Ala
            100                 105                 110 gtc caa gaa ggc ttc aac atg gag tac ggg atc gcg aca ttc gtc acc    384
Val Gln Glu Gly Phe Asn Met Glu Tyr Gly Ile Ala Thr Phe Val Thr
        115                 120                 125 tac gct gcc cac ctc gtc gat gga aac cca ctc acc aat ctc atc agc    432
Tyr Ala Ala His Leu Val Asp Gly Asn Pro Leu Thr Asn Leu Ile Ser
    130                 135                 140 att ggt ggg aag acg cgc aaa act ggc ccc gat cca cca cct ccc gcc    480
Ile Gly Gly Lys Thr Arg Lys Thr Gly Pro Asp Pro Pro Pro Pro Ala
145                 150                 155                 160 atc gtt ggt ggg ttg aac act cac gct gtt ttc gaa ggt gat gcg agt    528
Ile Val Gly Gly Leu Asn Thr His Ala Val Phe Glu Gly Asp Ala Ser
                165                 170                 175 atg acc cga ggc gac ttt cac ttg ggg gat aac ttc aac ttc aac cag    576
Met Thr Arg Gly Asp Phe His Leu Gly Asp Asn Phe Asn Phe Asn Gln
            180                 185                 190 acg ctt tgg gag cag ttc aag gac tac agt aac cgc tat gga ggt gga    624
Thr Leu Trp Glu Gln Phe Lys Asp Tyr Ser Asn Arg Tyr Gly Gly Gly
        195                 200                 205 cga tac aac cta act gcg gct gct gag ctt cgc tgg gca cgt atc cag    672
Arg Tyr Asn Leu Thr Ala Ala Ala Glu Leu Arg Trp Ala Arg Ile Gln
    210                 215                 220 caa tcc atg gcc acg aac ggt caa ttc gac ttc acc tcc cct cgg tac    720
Gln Ser Met Ala Thr Asn Gly Gln Phe Asp Phe Thr Ser Pro Arg Tyr
225                 230                 235                 240 ttc aca gcc tac gcc gaa tcc gtt ttc cca atc aac ttc ttc acg gac    768
Phe Thr Ala Tyr Ala Glu Ser Val Phe Pro Ile Asn Phe Phe Thr Asp
                245                 250                 255 gga cgg ctc ttc act tcg aac act acc gca cca ggc ccc gac atg gac    816
Gly Arg Leu Phe Thr Ser Asn Thr Thr Ala Pro Gly Pro Asp Met Asp
```

```
                260                 265                 270
tcg gcg ctc tcc ttc ttc cgg gac cac agg tac ccc aaa gac ttc cat     864
Ser Ala Leu Ser Phe Phe Arg Asp His Arg Tyr Pro Lys Asp Phe His
        275                 280                 285 cgc gca ccc gtt cca agt ggt gct cgt gga ctc gat gta gtc gcc gct     912
Arg Ala Pro Val Pro Ser Gly Ala Arg Gly Leu Asp Val Val Ala Ala
    290                 295                 300 gcc tac cct atc cag ccg ggc tac aat gca gat ggg aag gtg aac aac     960
Ala Tyr Pro Ile Gln Pro Gly Tyr Asn Ala Asp Gly Lys Val Asn Asn
305                 310                 315                 320 tac gtc ctc gac ccg act tcc gcg gat ttc aca aag ttc tgt ctg ctg    1008
Tyr Val Leu Asp Pro Thr Ser Ala Asp Phe Thr Lys Phe Cys Leu Leu
                325                 330                 335 tac gag aac ttt gtg ttg aag act gtg aag ggg ctc tat cca aat ccg    1056
Tyr Glu Asn Phe Val Leu Lys Thr Val Lys Gly Leu Tyr Pro Asn Pro
            340                 345                 350 aag ggc ttc ttg agg aag gca ctg gag aca aac ttg gaa tac ttt tac    1104
Lys Gly Phe Leu Arg Lys Ala Leu Glu Thr Asn Leu Glu Tyr Phe Tyr
        355                 360                 365 cag tcg ttc cct ggg tcg gga ggc tgc ccg cag gtc ttc ccc tgg ggc    1152
Gln Ser Phe Pro Gly Ser Gly Gly Cys Pro Gln Val Phe Pro Trp Gly
370                 375                 380 aag agt gat tag                                                    1164
Lys Ser Asp
385

<210> SEQ ID NO 8
<211> LENGTH: 387
<212> TYPE: PRT
<213> ORGANISM: Coprinopsis cinerea okayama7#130

<400> SEQUENCE: 8

Met Ile Ser Thr Ser Lys His Leu Phe Val Leu Leu Pro Leu Phe Leu
1               5                   10                  15

Val Ser His Leu Ser Leu Val Leu Gly Phe Pro Ala Tyr Ala Ser Leu
            20                  25                  30

Gly Gly Leu Thr Glu Arg Gln Val Glu Glu Tyr Thr Ser Lys Leu Pro
        35                  40                  45

Ile Val Phe Pro Pro Pro Pro Glu Pro Ile Lys Asp Pro Trp Leu
    50                  55                  60

Lys Leu Val Asn Asp Arg Ala His Pro Trp Arg Pro Leu Arg Arg Gly
65                  70                  75                  80

Asp Val Arg Gly Pro Cys Pro Gly Leu Asn Thr Leu Ala Ser His Gly
                85                  90                  95

Tyr Leu Pro Arg Asp Gly Val Ala Thr Pro Ala Gln Ile Ile Thr Ala
            100                 105                 110

Val Gln Glu Gly Phe Asn Met Glu Tyr Gly Ile Ala Thr Phe Val Thr
        115                 120                 125

Tyr Ala Ala His Leu Val Asp Gly Asn Pro Leu Thr Asn Leu Ile Ser
    130                 135                 140

Ile Gly Gly Lys Thr Arg Lys Thr Gly Pro Asp Pro Pro Pro Ala
145                 150                 155                 160

Ile Val Gly Gly Leu Asn Thr His Ala Val Phe Glu Gly Asp Ala Ser
                165                 170                 175

Met Thr Arg Gly Asp Phe His Leu Gly Asp Asn Phe Asn Phe Asn Gln
            180                 185                 190

Thr Leu Trp Glu Gln Phe Lys Asp Tyr Ser Asn Arg Tyr Gly Gly Gly
        195                 200                 205
```

```
Arg Tyr Asn Leu Thr Ala Ala Ala Glu Leu Arg Trp Ala Arg Ile Gln
    210                 215                 220

Gln Ser Met Ala Thr Asn Gly Gln Phe Asp Phe Thr Ser Pro Arg Tyr
225                 230                 235                 240

Phe Thr Ala Tyr Ala Glu Ser Val Phe Pro Ile Asn Phe Phe Thr Asp
                245                 250                 255

Gly Arg Leu Phe Thr Ser Asn Thr Thr Ala Pro Gly Pro Asp Met Asp
                260                 265                 270

Ser Ala Leu Ser Phe Phe Arg Asp His Arg Tyr Pro Lys Asp Phe His
            275                 280                 285

Arg Ala Pro Val Pro Ser Gly Ala Arg Gly Leu Asp Val Val Ala Ala
290                 295                 300

Ala Tyr Pro Ile Gln Pro Gly Tyr Asn Ala Asp Gly Lys Val Asn Asn
305                 310                 315                 320

Tyr Val Leu Asp Pro Thr Ser Ala Asp Phe Thr Lys Phe Cys Leu Leu
                325                 330                 335

Tyr Glu Asn Phe Val Leu Lys Thr Val Lys Gly Leu Tyr Pro Asn Pro
            340                 345                 350

Lys Gly Phe Leu Arg Lys Ala Leu Glu Thr Asn Leu Glu Tyr Phe Tyr
            355                 360                 365

Gln Ser Phe Pro Gly Ser Gly Gly Cys Pro Gln Val Phe Pro Trp Gly
370                 375                 380

Lys Ser Asp
385

<210> SEQ ID NO 9
<211> LENGTH: 1056
<212> TYPE: DNA
<213> ORGANISM: Coprinopsis cinerea okayama7#130
<220> FEATURE:
<221> NAME/KEY: CDS
<222> LOCATION: (1)..(1053)

<400> SEQUENCE: 9 atg gtt tcg tgc aag ctc cca ctc ccc ctc ctc act ctc gcc atc gct    48
Met Val Ser Cys Lys Leu Pro Leu Pro Leu Leu Thr Leu Ala Ile Ala
1               5                   10                  15 ttg gca aac gtt aat gcc ttt ccg gct tat cag tct ctt ggg ggt ctc    96
Leu Ala Asn Val Asn Ala Phe Pro Ala Tyr Gln Ser Leu Gly Gly Leu
            20                  25                  30 tcc aag cgc cag ctc gag acg att atc ccc gga ctg ccg gtt gtc aac    144
Ser Lys Arg Gln Leu Glu Thr Ile Ile Pro Gly Leu Pro Val Val Asn
        35                  40                  45 cct ggc cct cca cct ggg ccg tta gcg gat tcc acc ttg aag ttg gtc    192
Pro Gly Pro Pro Pro Gly Pro Leu Ala Asp Ser Thr Leu Lys Leu Val
    50                  55                  60 aat gat gcg gcg cat ccg tat cag gcg cct agg ccg cat ttg gat cat    240
Asn Asp Ala Ala His Pro Tyr Gln Ala Pro Arg Pro His Leu Asp His
65                  70                  75                  80 agg gga cct tgt ccg ggt ttg aat acg ttg gcg aat cat ggg tac ctt    288
Arg Gly Pro Cys Pro Gly Leu Asn Thr Leu Ala Asn His Gly Tyr Leu
                85                  90                  95 ccc agg tcg ggt atc gcg acg cca gct cag atc gtt cag gct gtt atg    336
Pro Arg Ser Gly Ile Ala Thr Pro Ala Gln Ile Val Gln Ala Val Met
            100                 105                 110 gaa gga ttc aac atg gag aac acg ttc gcg aaa ttc gtt acc tac gca    384
Glu Gly Phe Asn Met Glu Asn Thr Phe Ala Lys Phe Val Thr Tyr Ala
        115                 120                 125
```

```
gcc ttc ctc gtc gac gga aac ccg att acg aat ttg atg agt att gga        432
Ala Phe Leu Val Asp Gly Asn Pro Ile Thr Asn Leu Met Ser Ile Gly
    130                 135                 140 ggg aag act tgg agg acg ggg att att gaa ccc ccg cct cct gcg att        480
Gly Lys Thr Trp Arg Thr Gly Ile Ile Glu Pro Pro Pro Pro Ala Ile
145                 150                 155                 160 gtg ggt ggg ctg aat aca cat gct gtg ttt gaa ggt gat acg agt atg        528
Val Gly Gly Leu Asn Thr His Ala Val Phe Glu Gly Asp Thr Ser Met
                165                 170                 175 acg cgc gga gac ttc cat ttc ggc gat aat cat agt ttc aac cag acg        576
Thr Arg Gly Asp Phe His Phe Gly Asp Asn His Ser Phe Asn Gln Thr
            180                 185                 190 ttg ttc gat cag ttc gtg gaa tac agc aac atc cac gga gga gga ttc        624
Leu Phe Asp Gln Phe Val Glu Tyr Ser Asn Ile His Gly Gly Gly Phe
        195                 200                 205 tac aat ctc aca gct gca act gaa ctc cga tac cag cgc atc cag cag        672
Tyr Asn Leu Thr Ala Ala Thr Glu Leu Arg Tyr Gln Arg Ile Gln Gln
    210                 215                 220 tcg atc gct acg aac cca gag atg agt ttc gtc tct cct cgc tgg ttc        720
Ser Ile Ala Thr Asn Pro Glu Met Ser Phe Val Ser Pro Arg Trp Phe
225                 230                 235                 240 aca gca atc ctt ctt cag gac gag aag ttc cct gat gac ttc cat cgg        768
Thr Ala Ile Leu Leu Gln Asp Glu Lys Phe Pro Asp Asp Phe His Arg
                245                 250                 255 gcg cct ggt ccg ttc agc ttc gaa ggt cta ggg tac ctt gtt acg agg        816
Ala Pro Gly Pro Phe Ser Phe Glu Gly Leu Gly Tyr Leu Val Thr Arg
            260                 265                 270 cga cct atg cct cct gga aga aat gtt ggg gga gtg gac aat tat gtc        864
Arg Pro Met Pro Pro Gly Arg Asn Val Gly Gly Val Asp Asn Tyr Val
        275                 280                 285 cct gat ccc aac tcg gcg gat ttc aac tct ttc tgc aag atg tac gag        912
Pro Asp Pro Asn Ser Ala Asp Phe Asn Ser Phe Cys Lys Met Tyr Glu
    290                 295                 300 gac ttt gtg aac gat att gtc gtt gca ctc tat ccg aat ccg acg ggt        960
Asp Phe Val Asn Asp Ile Val Val Ala Leu Tyr Pro Asn Pro Thr Gly
305                 310                 315                 320 ttg ttg agg aga aat ttg atc aag aat ttg gag tac ttc tgg acg ggg       1008
Leu Leu Arg Arg Asn Leu Ile Lys Asn Leu Glu Tyr Phe Trp Thr Gly
                325                 330                 335 atg ttc gat cct gct tgc acc gaa gtg aaa ccg tat ggt aca ctg tag       1056
Met Phe Asp Pro Ala Cys Thr Glu Val Lys Pro Tyr Gly Thr Leu
            340                 345                 350

<210> SEQ ID NO 10
<211> LENGTH: 351
<212> TYPE: PRT
<213> ORGANISM: Coprinopsis cinerea okayama7#130

<400> SEQUENCE: 10

Met Val Ser Cys Lys Leu Pro Leu Pro Leu Leu Thr Leu Ala Ile Ala
1               5                   10                  15

Leu Ala Asn Val Asn Ala Phe Pro Ala Tyr Gln Ser Leu Gly Gly Leu
            20                  25                  30

Ser Lys Arg Gln Leu Glu Thr Ile Ile Pro Gly Leu Pro Val Val Asn
        35                  40                  45

Pro Gly Pro Pro Gly Pro Leu Ala Asp Ser Thr Leu Lys Leu Val
    50                  55                  60

Asn Asp Ala Ala His Pro Tyr Gln Ala Pro Arg Pro His Leu Asp His
65                  70                  75                  80

Arg Gly Pro Cys Pro Gly Leu Asn Thr Leu Ala Asn His Gly Tyr Leu
```

```
            85                  90                  95
Pro Arg Ser Gly Ile Ala Thr Pro Ala Gln Ile Val Gln Ala Val Met
        100                 105                 110

Glu Gly Phe Asn Met Glu Asn Thr Phe Ala Lys Phe Val Thr Tyr Ala
        115                 120                 125

Ala Phe Leu Val Asp Gly Asn Pro Ile Thr Asn Leu Met Ser Ile Gly
        130                 135                 140

Gly Lys Thr Trp Arg Thr Gly Ile Ile Glu Pro Pro Pro Ala Ile
145                 150                 155                 160

Val Gly Gly Leu Asn Thr His Ala Val Phe Glu Gly Asp Thr Ser Met
                165                 170                 175

Thr Arg Gly Asp Phe His Phe Gly Asp Asn His Ser Phe Asn Gln Thr
                180                 185                 190

Leu Phe Asp Gln Phe Val Glu Tyr Ser Asn Ile His Gly Gly Phe
        195                 200                 205

Tyr Asn Leu Thr Ala Ala Thr Glu Leu Arg Tyr Gln Arg Ile Gln Gln
        210                 215                 220

Ser Ile Ala Thr Asn Pro Glu Met Ser Phe Val Ser Pro Arg Trp Phe
225                 230                 235                 240

Thr Ala Ile Leu Leu Gln Asp Glu Lys Phe Pro Asp Phe His Arg
                245                 250                 255

Ala Pro Gly Pro Phe Ser Phe Glu Gly Leu Gly Tyr Leu Val Thr Arg
                260                 265                 270

Arg Pro Met Pro Pro Gly Arg Asn Val Gly Gly Val Asp Asn Tyr Val
        275                 280                 285

Pro Asp Pro Asn Ser Ala Asp Phe Asn Ser Phe Cys Lys Met Tyr Glu
        290                 295                 300

Asp Phe Val Asn Asp Ile Val Val Ala Leu Tyr Pro Asn Pro Thr Gly
305                 310                 315                 320

Leu Leu Arg Arg Asn Leu Ile Lys Asn Leu Tyr Phe Trp Thr Gly
                325                 330                 335

Met Phe Asp Pro Ala Cys Thr Glu Val Lys Pro Tyr Gly Thr Leu
                340                 345                 350

<210> SEQ ID NO 11
<211> LENGTH: 1161
<212> TYPE: DNA
<213> ORGANISM: Coprinopsis cinerea okayama7#130
<220> FEATURE:
<221> NAME/KEY: CDS
<222> LOCATION: (1)..(1158)

<400> SEQUENCE: 11 atg aac ggt ctg ttc gcc aca gtc aag ctt gcc ttg gtc act tta ctg      48
Met Asn Gly Leu Phe Ala Thr Val Lys Leu Ala Leu Val Thr Leu Leu
1               5                   10                  15 gct tcg caa agt caa ttc gcc aac gcc ttt ccg gca tgg caa tct ttg      96
Ala Ser Gln Ser Gln Phe Ala Asn Ala Phe Pro Ala Trp Gln Ser Leu
            20                  25                  30 ggc ggg cta tcg gag cga cag ttg gac gaa gtt atg ccg atg ctg aag     144
Gly Gly Leu Ser Glu Arg Gln Leu Asp Glu Val Met Pro Met Leu Lys
        35                  40                  45 cat cgc gtt cct cca cct cca cct ggc cct ccg gcc ttt act ggc gct     192
His Arg Val Pro Pro Pro Pro Pro Gly Pro Pro Ala Phe Thr Gly Ala
    50                  55                  60 aag ctc gtg aac gac aag gcc cat cca ttc aag cct ctc aaa aag ggc     240
Lys Leu Val Asn Asp Lys Ala His Pro Phe Lys Pro Leu Lys Lys Gly
65                  70                  75                  80
```

```
gac gtc cgt gga cca tgt cct gga ttg aac acc cta gcc tcc cat ggg        288
Asp Val Arg Gly Pro Cys Pro Gly Leu Asn Thr Leu Ala Ser His Gly
             85                  90                  95 tac ctc ccc cgc aac ggt gtc gcc agc cca tcc cag atc att gac gcc        336
Tyr Leu Pro Arg Asn Gly Val Ala Ser Pro Ser Gln Ile Ile Asp Ala
            100                 105                 110 gtc caa gaa ggt ttc aac atg gag aac gag ctg gct agg ttt acg acc        384
Val Gln Glu Gly Phe Asn Met Glu Asn Glu Leu Ala Arg Phe Thr Thr
        115                 120                 125 tat gtc gct cac ctc gtc gac ggc aac ctt gtc act gac ttg ctc agt        432
Tyr Val Ala His Leu Val Asp Gly Asn Leu Val Thr Asp Leu Leu Ser
    130                 135                 140 atc ggc gag aag acg cgc aag aca ggc ccc gat cct cct ccc cg gcc         480
Ile Gly Glu Lys Thr Arg Lys Thr Gly Pro Asp Pro Pro Pro Pro Ala
145                 150                 155                 160 atc gtc gga ggt ctc aac aac cac ggc acc ttc gaa gga gat gcc agt        528
Ile Val Gly Gly Leu Asn Asn His Gly Thr Phe Glu Gly Asp Ala Ser
                165                 170                 175 ttg acg cga ggc gac gcc ttc ttc ggc gat aat cac aac ttc aac cag        576
Leu Thr Arg Gly Asp Ala Phe Phe Gly Asp Asn His Asn Phe Asn Gln
            180                 185                 190 gag ctg ttt gac cag ttc aag aat ttc agc gcg gtg tac gga aac ggc        624
Glu Leu Phe Asp Gln Phe Lys Asn Phe Ser Ala Val Tyr Gly Asn Gly
        195                 200                 205 ttc ttc aac atg acc gtc gct ggg gag ctt cgc ttc cac cgc atc caa        672
Phe Phe Asn Met Thr Val Ala Gly Glu Leu Arg Phe His Arg Ile Gln
    210                 215                 220 caa tcc att gca acc aac ccc gag ttc tct ctc gtc gga ctg cgc cat        720
Gln Ser Ile Ala Thr Asn Pro Glu Phe Ser Leu Val Gly Leu Arg His
225                 230                 235                 240 ctc acc gcc tac gcg gaa gcc tcg ttc ccg tct ctc ttc gtc gat            768
Leu Thr Ala Tyr Ala Glu Ala Ser Phe Pro Ser Leu Phe Phe Val Asp
                245                 250                 255 ggg cga aag aca ggg gcc gaa gca ggg cag ctc gac atg gcc aca gcc        816
Gly Arg Lys Thr Gly Ala Glu Ala Gly Gln Leu Asp Met Ala Thr Ala
            260                 265                 270 gaa agc ttc ttc agg gac atg atg tac cct cct gat ttc ttc agg cct        864
Glu Ser Phe Phe Arg Asp Met Met Tyr Pro Pro Asp Phe Phe Arg Pro
        275                 280                 285 gca gcg cct gtt gct gga gat gcg gga gcc atc ttc ctc gct cac cct        912
Ala Ala Pro Val Ala Gly Asp Ala Gly Ala Ile Phe Leu Ala His Pro
    290                 295                 300 ttc caa cca gga agg aac gtc gga ggc gtc aac aac ttc acg gtg gat        960
Phe Gln Pro Gly Arg Asn Val Gly Gly Val Asn Asn Phe Thr Val Asp
305                 310                 315                 320 gac agc ttg ggc agt ctt ctc gat ttc tgc ggg ttc tac gag aac ttt       1008
Asp Ser Leu Gly Ser Leu Leu Asp Phe Cys Gly Phe Tyr Glu Asn Phe
                325                 330                 335 gtc aac aag acg ctc aag gca ctg tac ccc aac ccc aag ggc gtg ttg       1056
Val Asn Lys Thr Leu Lys Ala Leu Tyr Pro Asn Pro Lys Gly Val Leu
            340                 345                 350 agg agg aat ctc aat atc aac ctc cag ttc ttc ttc gag tcc ttg ccc       1104
Arg Arg Asn Leu Asn Ile Asn Leu Gln Phe Phe Phe Glu Ser Leu Pro
        355                 360                 365 aag gac gag agc ggt acc cct gtc tgc acc cag gtg ttc ccc tac gga       1152
Lys Asp Glu Ser Gly Thr Pro Val Cys Thr Gln Val Phe Pro Tyr Gly
    370                 375                 380 cgt aac tga                                                           1161
Arg Asn
385
```

<210> SEQ ID NO 12
<211> LENGTH: 386
<212> TYPE: PRT
<213> ORGANISM: Coprinopsis cinerea okayama7#130

<400> SEQUENCE: 12

| Met | Asn | Gly | Leu | Phe | Ala | Thr | Val | Lys | Leu | Ala | Leu | Val | Thr | Leu | Leu |
|-----|-----|-----|-----|-----|-----|-----|-----|-----|-----|-----|-----|-----|-----|-----|-----|
| 1 | | | | 5 | | | | | 10 | | | | | 15 | |
| Ala | Ser | Gln | Ser | Gln | Phe | Ala | Asn | Ala | Phe | Pro | Ala | Trp | Gln | Ser | Leu |
| | | | 20 | | | | | 25 | | | | | 30 | | |
| Gly | Gly | Leu | Ser | Glu | Arg | Gln | Leu | Asp | Glu | Val | Met | Pro | Met | Leu | Lys |
| | | 35 | | | | | 40 | | | | | 45 | | | |
| His | Arg | Val | Pro | Pro | Pro | Pro | Gly | Pro | Pro | Ala | Phe | Thr | Gly | Ala |
| | 50 | | | | | 55 | | | | | 60 | | | | |
| Lys | Leu | Val | Asn | Asp | Lys | Ala | His | Pro | Phe | Lys | Pro | Leu | Lys | Lys | Gly |
| 65 | | | | | 70 | | | | | 75 | | | | | 80 |
| Asp | Val | Arg | Gly | Pro | Cys | Pro | Gly | Leu | Asn | Thr | Leu | Ala | Ser | His | Gly |
| | | | | 85 | | | | | 90 | | | | | 95 | |
| Tyr | Leu | Pro | Arg | Asn | Gly | Val | Ala | Ser | Pro | Ser | Gln | Ile | Ile | Asp | Ala |
| | | | 100 | | | | | 105 | | | | | 110 | | |
| Val | Gln | Glu | Gly | Phe | Asn | Met | Glu | Asn | Glu | Leu | Ala | Arg | Phe | Thr | Thr |
| | | 115 | | | | | 120 | | | | | 125 | | | |
| Tyr | Val | Ala | His | Leu | Val | Asp | Gly | Asn | Leu | Val | Thr | Asp | Leu | Leu | Ser |
| | 130 | | | | | 135 | | | | | 140 | | | | |
| Ile | Gly | Glu | Lys | Thr | Arg | Lys | Thr | Gly | Pro | Asp | Pro | Pro | Pro | Pro | Ala |
| 145 | | | | | 150 | | | | | 155 | | | | | 160 |
| Ile | Val | Gly | Gly | Leu | Asn | Asn | His | Gly | Thr | Phe | Glu | Gly | Asp | Ala | Ser |
| | | | | 165 | | | | | 170 | | | | | 175 | |
| Leu | Thr | Arg | Gly | Asp | Ala | Phe | Phe | Gly | Asp | Asn | His | Asn | Phe | Asn | Gln |
| | | | 180 | | | | | 185 | | | | | 190 | | |
| Glu | Leu | Phe | Asp | Gln | Phe | Lys | Asn | Phe | Ser | Ala | Val | Tyr | Gly | Asn | Gly |
| | | 195 | | | | | 200 | | | | | 205 | | | |
| Phe | Phe | Asn | Met | Thr | Val | Ala | Gly | Glu | Leu | Arg | Phe | His | Arg | Ile | Gln |
| | 210 | | | | | 215 | | | | | 220 | | | | |
| Gln | Ser | Ile | Ala | Thr | Asn | Pro | Glu | Phe | Ser | Leu | Val | Gly | Leu | Arg | His |
| 225 | | | | | 230 | | | | | 235 | | | | | 240 |
| Leu | Thr | Ala | Tyr | Ala | Glu | Ala | Ser | Phe | Pro | Ser | Leu | Phe | Phe | Val | Asp |
| | | | | 245 | | | | | 250 | | | | | 255 | |
| Gly | Arg | Lys | Thr | Gly | Ala | Glu | Ala | Gly | Gln | Leu | Asp | Met | Ala | Thr | Ala |
| | | | 260 | | | | | 265 | | | | | 270 | | |
| Glu | Ser | Phe | Phe | Arg | Asp | Met | Met | Tyr | Pro | Pro | Asp | Phe | Phe | Arg | Pro |
| | | 275 | | | | | 280 | | | | | 285 | | | |
| Ala | Ala | Pro | Val | Ala | Gly | Asp | Ala | Gly | Ala | Ile | Phe | Leu | Ala | His | Pro |
| | 290 | | | | | 295 | | | | | 300 | | | | |
| Phe | Gln | Pro | Gly | Arg | Asn | Val | Gly | Gly | Val | Asn | Asn | Phe | Thr | Val | Asp |
| 305 | | | | | 310 | | | | | 315 | | | | | 320 |
| Asp | Ser | Leu | Gly | Ser | Leu | Leu | Asp | Phe | Cys | Gly | Phe | Tyr | Glu | Asn | Phe |
| | | | | 325 | | | | | 330 | | | | | 335 | |
| Val | Asn | Lys | Thr | Leu | Lys | Ala | Leu | Tyr | Pro | Asn | Pro | Lys | Gly | Val | Leu |
| | | | 340 | | | | | 345 | | | | | 350 | | |
| Arg | Arg | Asn | Leu | Asn | Ile | Asn | Leu | Gln | Phe | Phe | Glu | Ser | Leu | Pro |
| | | 355 | | | | | 360 | | | | | 365 | | | |
| Lys | Asp | Glu | Ser | Gly | Thr | Pro | Val | Cys | Thr | Gln | Val | Phe | Pro | Tyr | Gly |
| | 370 | | | | | 375 | | | | | 380 | | | | |

Arg Asn
385

<210> SEQ ID NO 13
<211> LENGTH: 1026
<212> TYPE: DNA
<213> ORGANISM: Coprinopsis cinerea okayama7#130
<220> FEATURE:
<221> NAME/KEY: CDS
<222> LOCATION: (1)..(1023)

<400> SEQUENCE: 13

| | | | | | | | | | | | | | | | | |
|---|---|---|---|---|---|---|---|---|---|---|---|---|---|---|---|---|
| atg | ctc | aaa | ccg | cgt | gtt | cca | ccc | cct | ccc | cct | ggc | cct | ttg | gcg | ttc | 48 |
| Met | Leu | Lys | Pro | Arg | Val | Pro | Pro | Pro | Pro | Pro | Gly | Pro | Leu | Ala | Phe | |
| 1 | | | | 5 | | | | | 10 | | | | | 15 | | |
| aat | gga | acc | aag | ctt | gtg | aac | gac | gaa | gat | cac | cct | ttc | atg | cct | ccg | 96 |
| Asn | Gly | Thr | Lys | Leu | Val | Asn | Asp | Glu | Asp | His | Pro | Phe | Met | Pro | Pro | |
| | | | 20 | | | | | 25 | | | | | 30 | | | |
| agg | aag | ggg | gat | gcc | cgt | gga | ccg | tgt | cct | ggg | ttg | aat | act | ttg | gcg | 144 |
| Arg | Lys | Gly | Asp | Ala | Arg | Gly | Pro | Cys | Pro | Gly | Leu | Asn | Thr | Leu | Ala | |
| | | 35 | | | | | 40 | | | | | 45 | | | | |
| tcg | cac | ggg | tac | ctc | ccc | cgt | aat | ggc | ata | gcc | act | ccc | gct | cag | atc | 192 |
| Ser | His | Gly | Tyr | Leu | Pro | Arg | Asn | Gly | Ile | Ala | Thr | Pro | Ala | Gln | Ile | |
| 50 | | | | | 55 | | | | | 60 | | | | | | |
| atc | aac | gcc | gtt | caa | gaa | ggc | ttc | aat | atg | gag | aac | gag | atc | gcc | agg | 240 |
| Ile | Asn | Ala | Val | Gln | Glu | Gly | Phe | Asn | Met | Glu | Asn | Glu | Ile | Ala | Arg | |
| 65 | | | | | 70 | | | | | 75 | | | | | 80 | |
| ttc | acg | acc | tac | acc | gcg | cat | ctc | atg | gac | ggg | aat | ctg | gtc | act | gac | 288 |
| Phe | Thr | Thr | Tyr | Thr | Ala | His | Leu | Met | Asp | Gly | Asn | Leu | Val | Thr | Asp | |
| | | | | 85 | | | | | 90 | | | | | 95 | | |
| ttg | ctc | agt | atc | ggg | ccg | aag | acg | ccc | aag | act | gga | cct | gac | cca | cct | 336 |
| Leu | Leu | Ser | Ile | Gly | Pro | Lys | Thr | Pro | Lys | Thr | Gly | Pro | Asp | Pro | Pro | |
| | | | 100 | | | | | 105 | | | | | 110 | | | |
| ccc | cct | gcc | atc | gtt | gga | gga | ttg | aac | aac | cat | ggt | act | ttc | gaa | ggc | 384 |
| Pro | Pro | Ala | Ile | Val | Gly | Gly | Leu | Asn | Asn | His | Gly | Thr | Phe | Glu | Gly | |
| | | 115 | | | | | 120 | | | | | 125 | | | | |
| gac | gcg | agt | ctg | tct | cgg | gca | gac | gct | ttc | ttt | ggc | gat | aac | cat | agc | 432 |
| Asp | Ala | Ser | Leu | Ser | Arg | Ala | Asp | Ala | Phe | Phe | Gly | Asp | Asn | His | Ser | |
| 130 | | | | | 135 | | | | | 140 | | | | | | |
| ttt | gac | caa | gag | ctg | ttc | gac | cag | ttc | agg | aat | ttc | agc | gcg | atc | tac | 480 |
| Phe | Asp | Gln | Glu | Leu | Phe | Asp | Gln | Phe | Arg | Asn | Phe | Ser | Ala | Ile | Tyr | |
| 145 | | | | | 150 | | | | | 155 | | | | | 160 | |
| gga | aac | ggt | ttc | ttc | aat | atg | aca | gtc | gcc | gcc | gag | ctc | agg | ttc | cac | 528 |
| Gly | Asn | Gly | Phe | Phe | Asn | Met | Thr | Val | Ala | Ala | Glu | Leu | Arg | Phe | His | |
| | | | | 165 | | | | | 170 | | | | | 175 | | |
| cgt | atc | caa | cag | tcc | atc | gct | acc | aac | ccc | gaa | ttc | tcc | ttc | gct | gga | 576 |
| Arg | Ile | Gln | Gln | Ser | Ile | Ala | Thr | Asn | Pro | Glu | Phe | Ser | Phe | Ala | Gly | |
| | | | 180 | | | | | 185 | | | | | 190 | | | |
| ctc | cgt | cac | att | acc | gcc | tac | gct | gaa | gcc | tct | ttc | cct | ccg | atc | ttc | 624 |
| Leu | Arg | His | Ile | Thr | Ala | Tyr | Ala | Glu | Ala | Ser | Phe | Pro | Pro | Ile | Phe | |
| | | 195 | | | | | 200 | | | | | 205 | | | | |
| ttc | gtc | gat | ggg | cgg | aag | acc | ggt | gct | gag | gcg | gga | caa | ctc | gac | atg | 672 |
| Phe | Val | Asp | Gly | Arg | Lys | Thr | Gly | Ala | Glu | Ala | Gly | Gln | Leu | Asp | Met | |
| | 210 | | | | | 215 | | | | | 220 | | | | | |
| gcc | gcc | gcg | gag | agc | ttc | ttc | aag | cac | atg | atg | tac | cct | ccc | gac | ttc | 720 |
| Ala | Ala | Ala | Glu | Ser | Phe | Phe | Lys | His | Met | Met | Tyr | Pro | Pro | Asp | Phe | |
| 225 | | | | | 230 | | | | | 235 | | | | | 240 | |
| cac | cgc | cct | gcg | gaa | ccc | gtc | aac | agc | gat | gcg | cag | gcc | gta | ttt | gaa | 768 |
| His | Arg | Pro | Ala | Glu | Pro | Val | Asn | Ser | Asp | Ala | Gln | Ala | Val | Phe | Glu | |
| | | | | 245 | | | | | 250 | | | | | 255 | | |
| gtt | cat | cct | ttc | caa | ccc | ggg | agg | aac | gtc | gga | ggg | gtc | aac | aac | tat | 816 |

```
Val His Pro Phe Gln Pro Gly Arg Asn Val Gly Gly Val Asn Asn Tyr
                260                 265                 270 acc gtt gat gag agt ttg ggt ggt ctg ttg gat ttc tgc ggg ttc tac     864
Thr Val Asp Glu Ser Leu Gly Gly Leu Leu Asp Phe Cys Gly Phe Tyr
            275                 280                 285 gag aac ttt gtg aac aag acg atc aag ggt ttg tat ccc aac ccc acg     912
Glu Asn Phe Val Asn Lys Thr Ile Lys Gly Leu Tyr Pro Asn Pro Thr
290                 295                 300 ggc gtt ttg aag agg aat ttg aat att aat ctc gat ttc ctc ttt gag     960
Gly Val Leu Lys Arg Asn Leu Asn Ile Asn Leu Asp Phe Leu Phe Glu
305                 310                 315                 320 gcg ttg ccg aag gct ggt gac ggg tct caa ccg tgt act caa gtt ttc    1008
Ala Leu Pro Lys Ala Gly Asp Gly Ser Gln Pro Cys Thr Gln Val Phe
                325                 330                 335 cct tac gga cac gat tag                                             1026
Pro Tyr Gly His Asp
                340

<210> SEQ ID NO 14
<211> LENGTH: 341
<212> TYPE: PRT
<213> ORGANISM: Coprinopsis cinerea okayama7#130

<400> SEQUENCE: 14

Met Leu Lys Pro Arg Val Pro Pro Pro Gly Pro Leu Ala Phe
1               5                   10                  15

Asn Gly Thr Lys Leu Val Asn Asp Glu Asp His Pro Phe Met Pro Pro
                20                  25                  30

Arg Lys Gly Asp Ala Arg Gly Pro Cys Pro Gly Leu Asn Thr Leu Ala
            35                  40                  45

Ser His Gly Tyr Leu Pro Arg Asn Gly Ile Ala Thr Pro Ala Gln Ile
        50                  55                  60

Ile Asn Ala Val Gln Glu Gly Phe Asn Met Glu Asn Glu Ile Ala Arg
65                  70                  75                  80

Phe Thr Thr Tyr Thr Ala His Leu Met Asp Gly Asn Leu Val Thr Asp
                85                  90                  95

Leu Leu Ser Ile Gly Pro Lys Thr Pro Lys Thr Gly Pro Asp Pro Pro
            100                 105                 110

Pro Pro Ala Ile Val Gly Gly Leu Asn Asn His Gly Thr Phe Glu Gly
        115                 120                 125

Asp Ala Ser Leu Ser Arg Ala Asp Ala Phe Phe Gly Asp Asn His Ser
    130                 135                 140

Phe Asp Gln Glu Leu Phe Asp Gln Phe Arg Asn Phe Ser Ala Ile Tyr
145                 150                 155                 160

Gly Asn Gly Phe Phe Asn Met Thr Val Ala Ala Glu Leu Arg Phe His
                165                 170                 175

Arg Ile Gln Gln Ser Ile Ala Thr Asn Pro Glu Phe Ser Phe Ala Gly
            180                 185                 190

Leu Arg His Ile Thr Ala Tyr Ala Glu Ala Ser Phe Pro Ile Phe
        195                 200                 205

Phe Val Asp Gly Arg Lys Thr Gly Ala Glu Ala Gly Gln Leu Asp Met
    210                 215                 220

Ala Ala Ala Glu Ser Phe Phe Lys His Met Met Tyr Pro Pro Asp Phe
225                 230                 235                 240

His Arg Pro Ala Glu Pro Val Asn Ser Asp Ala Gln Ala Val Phe Glu
                245                 250                 255

Val His Pro Phe Gln Pro Gly Arg Asn Val Gly Gly Val Asn Asn Tyr
```

```
              260                 265                 270
Thr Val Asp Glu Ser Leu Gly Gly Leu Leu Asp Phe Cys Gly Phe Tyr
            275                 280                 285

Glu Asn Phe Val Asn Lys Thr Ile Lys Gly Leu Tyr Pro Asn Pro Thr
            290                 295                 300

Gly Val Leu Lys Arg Asn Leu Asn Ile Asn Leu Asp Phe Leu Phe Glu
305                 310                 315                 320

Ala Leu Pro Lys Ala Gly Asp Gly Ser Gln Pro Cys Thr Gln Val Phe
                325                 330                 335

Pro Tyr Gly His Asp
            340

<210> SEQ ID NO 15
<211> LENGTH: 687
<212> TYPE: DNA
<213> ORGANISM: Coprinus radians
<220> FEATURE:
<221> NAME/KEY: CDS
<222> LOCATION: (1)..(687)

<400> SEQUENCE: 15 ccg cct ccg gaa tac gtc gga cca aag ctc gtc aat gac gca gac cac      48
Pro Pro Pro Glu Tyr Val Gly Pro Lys Leu Val Asn Asp Ala Asp His
1               5                  10                  15 cct tgg gag cct ctt cga cct gga gat att cgt ggc ccg tgc cca gga      96
Pro Trp Glu Pro Leu Arg Pro Gly Asp Ile Arg Gly Pro Cys Pro Gly
            20                  25                  30 ctc aat acc ctt gcg tct cat ggt tat ctg ccg cgc aac gga gtg gcg     144
Leu Asn Thr Leu Ala Ser His Gly Tyr Leu Pro Arg Asn Gly Val Ala
        35                  40                  45 act ccc gct caa atc att aat gca att gtg gaa ggc ttc aac ttc aac     192
Thr Pro Ala Gln Ile Ile Asn Ala Ile Val Glu Gly Phe Asn Phe Asn
    50                  55                  60 tac gaa ggc gca gtc ttc gtc acg tac ttc gct cat atc gtc gac gga     240
Tyr Glu Gly Ala Val Phe Val Thr Tyr Phe Ala His Ile Val Asp Gly
65                  70                  75                  80 aac ctc gtc act gat ctt ctc agt att gga gga aag acc aat ctg act     288
Asn Leu Val Thr Asp Leu Leu Ser Ile Gly Gly Lys Thr Asn Leu Thr
                85                  90                  95 ggc gag gac acc gga gcc cca gcc ata atc gga ggg ttg aac acg cac     336
Gly Glu Asp Thr Gly Ala Pro Ala Ile Ile Gly Gly Leu Asn Thr His
            100                 105                 110 tct gtc ttt gaa ggc gac gca agc atg act cgc gat gac ttc cac ttt     384
Ser Val Phe Glu Gly Asp Ala Ser Met Thr Arg Asp Asp Phe His Phe
        115                 120                 125 ggt gac aac cac agc ttc aac cag acc ttg ttc gac cag ttc gtc gag     432
Gly Asp Asn His Ser Phe Asn Gln Thr Leu Phe Asp Gln Phe Val Glu
    130                 135                 140 tac agc aac acc tac ggc ggt ggc ttc tat aac caa gaa gtt gca ggc     480
Tyr Ser Asn Thr Tyr Gly Gly Gly Phe Tyr Asn Gln Glu Val Ala Gly
145                 150                 155                 160 cac ctc cgc cgt cgc cgt atc gag caa tcc att gcc acc aac ccc gaa     528
His Leu Arg Arg Arg Arg Ile Glu Gln Ser Ile Ala Thr Asn Pro Glu
                165                 170                 175 ttc gac ttc acc tct ccc cgt ttc ttc aca gcc ttc gcc gag tcc agc     576
Phe Asp Phe Thr Ser Pro Arg Phe Phe Thr Ala Phe Ala Glu Ser Ser
            180                 185                 190 ttc cct tac tcg ttc ttc gtc gac ggc cgt atc acc gag cgt ccc gga     624
Phe Pro Tyr Ser Phe Phe Val Asp Gly Arg Ile Thr Glu Arg Pro Gly
        195                 200                 205
```

```
ggt ctc agt atg gag aat gcc act ctc ttc ttc agg gac cac aag atg      672
Gly Leu Ser Met Glu Asn Ala Thr Leu Phe Phe Arg Asp His Lys Met
    210                 215                 220 cca gac gac ttc tgg                                                   687
Pro Asp Asp Phe Trp
225
```

<210> SEQ ID NO 16
<211> LENGTH: 229
<212> TYPE: PRT
<213> ORGANISM: Coprinus radians

<400> SEQUENCE: 16

```
Pro Pro Pro Glu Tyr Val Gly Pro Lys Leu Val Asn Asp Ala Asp His
1               5                   10                  15

Pro Trp Glu Pro Leu Arg Pro Gly Asp Ile Arg Gly Pro Cys Pro Gly
            20                  25                  30

Leu Asn Thr Leu Ala Ser His Gly Tyr Leu Pro Arg Asn Gly Val Ala
        35                  40                  45

Thr Pro Ala Gln Ile Ile Asn Ala Ile Val Glu Gly Phe Asn Phe Asn
    50                  55                  60

Tyr Glu Gly Ala Val Phe Val Thr Tyr Phe Ala His Ile Val Asp Gly
65                  70                  75                  80

Asn Leu Val Thr Asp Leu Leu Ser Ile Gly Gly Lys Thr Asn Leu Thr
                85                  90                  95

Gly Glu Asp Thr Gly Ala Pro Ala Ile Ile Gly Gly Leu Asn Thr His
            100                 105                 110

Ser Val Phe Glu Gly Asp Ala Ser Met Thr Arg Asp Asp Phe His Phe
        115                 120                 125

Gly Asp Asn His Ser Phe Asn Gln Thr Leu Phe Asp Gln Phe Val Glu
    130                 135                 140

Tyr Ser Asn Thr Tyr Gly Gly Gly Phe Tyr Asn Gln Glu Val Ala Gly
145                 150                 155                 160

His Leu Arg Arg Arg Arg Ile Glu Gln Ser Ile Ala Thr Asn Pro Glu
                165                 170                 175

Phe Asp Phe Thr Ser Pro Arg Phe Phe Thr Ala Phe Ala Glu Ser Ser
            180                 185                 190

Phe Pro Tyr Ser Phe Phe Val Asp Gly Arg Ile Thr Glu Arg Pro Gly
        195                 200                 205

Gly Leu Ser Met Glu Asn Ala Thr Leu Phe Phe Arg Asp His Lys Met
    210                 215                 220

Pro Asp Asp Phe Trp
225
```

<210> SEQ ID NO 17
<211> LENGTH: 489
<212> TYPE: DNA
<213> ORGANISM: Coprinus radians
<220> FEATURE:
<221> NAME/KEY: CDS
<222> LOCATION: (1)..(315)

<400> SEQUENCE: 17

```
gac cac aag atg ccc gac gac ttc tgg cgt gcc ccc gag ccc act ggg      48
Asp His Lys Met Pro Asp Asp Phe Trp Arg Ala Pro Glu Pro Thr Gly
1               5                   10                  15 gga ctc aac gtc ctc gac atc tac aga gca tct ggc tct cct cct gcc      96
Gly Leu Asn Val Leu Asp Ile Tyr Arg Ala Ser Gly Ser Pro Pro Ala
            20                  25                  30
```

```
gga cgc aac gtc aac ggc acc aac acg ttc acc ccc gat ccc aac agc    144
Gly Arg Asn Val Asn Gly Thr Asn Thr Phe Thr Pro Asp Pro Asn Ser
        35                  40                  45 gcg gat ttc gat aat cct tgt gaa ctc tac tac gac tac gtc aac agg    192
Ala Asp Phe Asp Asn Pro Cys Glu Leu Tyr Tyr Asp Tyr Val Asn Arg
 50                  55                  60 ata gtg aag agt ctt tac ccc aac ccc act ggg atc ctc agg gac aac    240
Ile Val Lys Ser Leu Tyr Pro Asn Pro Thr Gly Ile Leu Arg Asp Asn
 65                  70                  75                  80 ctg aat atc gcc ctc ggg cat gtg ttt gac tcc atg gac ttc ggc gat    288
Leu Asn Ile Ala Leu Gly His Val Phe Asp Ser Met Asp Phe Gly Asp
                 85                  90                  95 tgc gag cag ttg ttc cct tat ggg cgc taggtccgtg tatatagatt          335
Cys Glu Gln Leu Phe Pro Tyr Gly Arg
            100                 105 tgccgaggtt ctattaccct atccttctgc tgcctccgag cttcatttta ggctcgtcct  395
gtcctttaca tagatgttgt tttggtcgtt gctttgacca atatacattc ctcagtctaa  455
aaaaaaaaaa aaaagcact gatacgcggt taca                              489

<210> SEQ ID NO 18
<211> LENGTH: 105
<212> TYPE: PRT
<213> ORGANISM: Coprinus radians

<400> SEQUENCE: 18

Asp His Lys Met Pro Asp Asp Phe Trp Arg Ala Pro Glu Pro Thr Gly
1               5                   10                  15

Gly Leu Asn Val Leu Asp Ile Tyr Arg Ala Ser Gly Ser Pro Pro Ala
            20                  25                  30

Gly Arg Asn Val Asn Gly Thr Asn Thr Phe Thr Pro Asp Pro Asn Ser
        35                  40                  45

Ala Asp Phe Asp Asn Pro Cys Glu Leu Tyr Tyr Asp Tyr Val Asn Arg
 50                  55                  60

Ile Val Lys Ser Leu Tyr Pro Asn Pro Thr Gly Ile Leu Arg Asp Asn
 65                  70                  75                  80

Leu Asn Ile Ala Leu Gly His Val Phe Asp Ser Met Asp Phe Gly Asp
                 85                  90                  95

Cys Glu Gln Leu Phe Pro Tyr Gly Arg
            100                 105

<210> SEQ ID NO 19
<211> LENGTH: 325
<212> TYPE: PRT
<213> ORGANISM: Coprinus radians DSM888

<400> SEQUENCE: 19

Pro Pro Pro Glu Tyr Val Gly Pro Lys Leu Val Asn Asp Ala Asp His
1               5                   10                  15

Pro Trp Glu Pro Leu Arg Pro Gly Asp Ile Arg Gly Pro Cys Pro Gly
            20                  25                  30

Leu Asn Thr Leu Ala Ser His Gly Tyr Leu Pro Arg Asn Gly Val Ala
        35                  40                  45

Thr Pro Ala Gln Ile Ile Asn Ala Ile Val Glu Gly Phe Asn Phe Asn
 50                  55                  60

Tyr Glu Gly Ala Val Phe Val Thr Tyr Phe Ala His Ile Val Asp Gly
 65                  70                  75                  80

Asn Leu Val Thr Asp Leu Leu Ser Ile Gly Gly Lys Thr Asn Leu Thr
                 85                  90                  95
```

```
Gly Glu Asp Thr Gly Ala Pro Ala Ile Ile Gly Gly Leu Asn Thr His
            100                 105                 110

Ser Val Phe Glu Gly Asp Ala Ser Met Thr Arg Asp Phe His Phe
        115                 120                 125

Gly Asp Asn His Ser Phe Asn Gln Thr Leu Phe Asp Gln Phe Val Glu
    130                 135                 140

Tyr Ser Asn Thr Tyr Gly Gly Phe Tyr Asn Gln Glu Val Ala Gly
145                 150                 155                 160

His Leu Arg Arg Arg Ile Glu Gln Ser Ile Ala Thr Asn Pro Glu
            165                 170                 175

Phe Asp Phe Thr Ser Pro Arg Phe Phe Thr Ala Phe Ala Glu Ser Ser
        180                 185                 190

Phe Pro Tyr Ser Phe Phe Val Asp Gly Arg Ile Thr Glu Arg Pro Gly
            195                 200                 205

Gly Leu Ser Met Glu Asn Ala Thr Leu Phe Phe Arg Asp His Lys Met
    210                 215                 220

Pro Asp Asp Phe Trp Arg Ala Pro Glu Pro Thr Gly Gly Leu Asn Val
225                 230                 235                 240

Leu Asp Ile Tyr Arg Ala Ser Gly Ser Pro Pro Ala Gly Arg Asn Val
            245                 250                 255

Asn Gly Thr Asn Thr Phe Thr Pro Asp Pro Asn Ser Ala Asp Phe Asp
        260                 265                 270

Asn Pro Cys Glu Leu Tyr Tyr Asp Tyr Val Asn Arg Ile Val Lys Ser
            275                 280                 285

Leu Tyr Pro Asn Pro Thr Gly Ile Leu Arg Asp Asn Leu Asn Ile Ala
        290                 295                 300

Leu Gly His Val Phe Asp Ser Met Asp Phe Gly Asp Cys Glu Gln Leu
305                 310                 315                 320

Phe Pro Tyr Gly Arg
            325

<210> SEQ ID NO 20
<211> LENGTH: 36
<212> TYPE: DNA
<213> ORGANISM: Artificial sequence
<220> FEATURE:
<223> OTHER INFORMATION: polyT-anchor-primer

<400> SEQUENCE: 20
tagctcgatg cttgcacgct tttttttttt tttttt                              36

<210> SEQ ID NO 21
<211> LENGTH: 19
<212> TYPE: DNA
<213> ORGANISM: Artificial sequence
<220> FEATURE:
<223> OTHER INFORMATION: AP-primer

<400> SEQUENCE: 21
tagctcgatg cttgcacgc                                                 19

<210> SEQ ID NO 22
<211> LENGTH: 37
<212> TYPE: DNA
<213> ORGANISM: Artificial sequence
<220> FEATURE:
<223> OTHER INFORMATION: polyT-anchor2-primer

<400> SEQUENCE: 22
```

-continued tgtaaccgcg tatcagtgct tttttttttt tttttv                            37

<210> SEQ ID NO 23
<211> LENGTH: 19
<212> TYPE: DNA
<213> ORGANISM: Artificial sequence
<220> FEATURE:
<223> OTHER INFORMATION: AP2-primer

<400> SEQUENCE: 23
tgtaaccgcg tatcagtgc                                               19

<210> SEQ ID NO 24
<211> LENGTH: 30
<212> TYPE: DNA
<213> ORGANISM: Artificial sequence
<220> FEATURE:
<223> OTHER INFORMATION: TS-short-primer
<220> FEATURE:
<221> NAME/KEY: misc_feature
<222> LOCATION: (28)..(30)
<223> OTHER INFORMATION: The nucleotides 'n' in positions 28-30 are
      ribonucleotide guanosine 'rG'.

<400> SEQUENCE: 24
aagcagtggt atcaacgcag agtacgcnnn                                   30

<210> SEQ ID NO 25
<211> LENGTH: 45
<212> TYPE: DNA
<213> ORGANISM: Artificial sequence
<220> FEATURE:
<223> OTHER INFORMATION: heel-carrier primer

<400> SEQUENCE: 25
gtaatacgac tcactatagg gcaagcagtg gtatcaacgc agagt                  45

<210> SEQ ID NO 26
<211> LENGTH: 22
<212> TYPE: DNA
<213> ORGANISM: Artificial sequence
<220> FEATURE:
<223> OTHER INFORMATION: heel-specific primer

<400> SEQUENCE: 26
gtaatacgac tcactatagg gc                                           22

<210> SEQ ID NO 27
<211> LENGTH: 15
<212> TYPE: DNA
<213> ORGANISM: Artificial sequence
<220> FEATURE:
<223> OTHER INFORMATION: Primer Cop1-For
<220> FEATURE:
<221> NAME/KEY: misc_feature
<222> LOCATION: (5)..(5)
<223> OTHER INFORMATION: n is a, c, g, or t

<400> SEQUENCE: 27
ccccnccgar taygt                                                   15

<210> SEQ ID NO 28
<211> LENGTH: 14
<212> TYPE: DNA
<213> ORGANISM: Artificial sequence
<220> FEATURE:
<223> OTHER INFORMATION: Primer Cop5-For

<400> SEQUENCE: 28

```
gaycayaara tgcc                                                       14
```

<210> SEQ ID NO 29
<211> LENGTH: 18
<212> TYPE: DNA
<213> ORGANISM: Artificial sequence
<220> FEATURE:
<223> OTHER INFORMATION: Primer Cop6-Rev
<220> FEATURE:
<221> NAME/KEY: misc_feature
<222> LOCATION: (13)..(13)
<223> OTHER INFORMATION: n is a, c, g, or t

<400> SEQUENCE: 29

```
ccaraartcr tcnggcat                                                   18
```

<210> SEQ ID NO 30
<211> LENGTH: 20
<212> TYPE: DNA
<213> ORGANISM: Artificial sequence
<220> FEATURE:
<223> OTHER INFORMATION: Primer Aap1-For
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 30

```
garccggnaa rccccggncc                                                 20
```

<210> SEQ ID NO 31
<211> LENGTH: 17
<212> TYPE: DNA
<213> ORGANISM: Artificial sequence
<220> FEATURE:
<223> OTHER INFORMATION: Primer Aap2-Rev
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 31

```
gcarngtrtt arccngg                                                    17
```

<210> SEQ ID NO 32
<211> LENGTH: 15
<212> TYPE: DNA
<213> ORGANISM: Artificial sequence
<220> FEATURE:
<223> OTHER INFORMATION: Primer Aap4-For
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 32

```
aaygcacnaa yccng                                                      15
```

```
<210> SEQ ID NO 33
<211> LENGTH: 16
<212> TYPE: DNA
<213> ORGANISM: Artificial sequence
<220> FEATURE:
<223> OTHER INFORMATION: Primer Aap4-Rev
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 33
aartcggrtt ngtngc                                               16

<210> SEQ ID NO 34
<211> LENGTH: 15
<212> TYPE: DNA
<213> ORGANISM: Artificial sequence
<220> FEATURE:
<223> OTHER INFORMATION: Primer Aap6-Rev
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 34
arccngtggr ttngg                                                15

<210> SEQ ID NO 35
<211> LENGTH: 21
<212> TYPE: DNA
<213> ORGANISM: Artificial sequence
<220> FEATURE:
<223> OTHER INFORMATION: Specific primer 1Aap-For1

<400> SEQUENCE: 35
cgcaacatga aatacttcag c                                         21

<210> SEQ ID NO 36
<211> LENGTH: 22
<212> TYPE: DNA
<213> ORGANISM: Artificial sequence
<220> FEATURE:
<223> OTHER INFORMATION: Specific primer 1Aap-For2

<400> SEQUENCE: 36
gagccaacac aacctcctgg ac                                        22

<210> SEQ ID NO 37
<211> LENGTH: 21
<212> TYPE: DNA
<213> ORGANISM: Artificial sequence
<220> FEATURE:
<223> OTHER INFORMATION: Specific primer 1Aap-Rev4

<400> SEQUENCE: 37
ggcataaggt cactggagtc c                                         21

<210> SEQ ID NO 38
<211> LENGTH: 20
<212> TYPE: DNA
<213> ORGANISM: Artificial sequence
```

```
<220> FEATURE:
<223> OTHER INFORMATION: Specific primer 2Aap-For1

<400> SEQUENCE: 38
ttctacatga aatattttcc                                                         20

<210> SEQ ID NO 39
<211> LENGTH: 18
<212> TYPE: DNA
<213> ORGANISM: Artificial sequence
<220> FEATURE:
<223> OTHER INFORMATION: Specific primer 2Aap-Rev2

<400> SEQUENCE: 39
aagcaggttg ttggaccg                                                           18

<210> SEQ ID NO 40
<211> LENGTH: 14
<212> TYPE: PRT
<213> ORGANISM: Artificial sequence
<220> FEATURE:
<223> OTHER INFORMATION: Peroxygenase motif I
<220> FEATURE:
<221> NAME/KEY: VARIANT
<222> LOCATION: (1)..(1)
<223> OTHER INFORMATION: The amino acid may be Phe or Lys.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: The amino acid may be Tyr or Phe.
<220> FEATURE:
<221> NAME/KEY: VARIANT
<222> LOCATION: (6)..(6)
<223> OTHER INFORMATION: The amino acid may be Ala or Asn.
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: The amino acid may be Phe, His or Tyr.
<220> FEATURE:
<221> NAME/KEY: VARIANT
<222> LOCATION: (10)..(10)
<223> OTHER INFORMATION: The amino acid may be Gly or Asn.
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: The amino acid may be Tyr or Phe.

<400> SEQUENCE: 40

Xaa Xaa Xaa Xaa Ser Xaa Xaa Xaa Gly Xaa Gly Xaa Xaa Asn
1               5                   10

<210> SEQ ID NO 41
<211> LENGTH: 14
<212> TYPE: PRT
<213> ORGANISM: Artificial sequence
<220> FEATURE:
<223> OTHER INFORMATION: Peroxygenase motif II
<220> FEATURE:
<221> NAME/KEY: VARIANT
<222> LOCATION: (2)..(2)
<223> OTHER INFORMATION: The amino acid may be Gly or Asn.
<220> FEATURE:
```

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: The amino acid may be Tyr or Phe.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: The amino acid may be Val or Ala.
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: The amino acid may be Glu or His.
<220> FEATURE:
<221> NAME/KEY: VARIANT
<222> LOCATION: (13)..(13)
<223> OTHER INFORMATION: The amino acid may be Leu or Phe.

<400> SEQUENCE: 41

Gly Xaa Gly Xaa Xaa Asn Xaa Xaa Xaa Ala Xaa Xaa Xaa Arg
1               5                   10

<210> SEQ ID NO 42
<211> LENGTH: 12
<212> TYPE: PRT
<213> ORGANISM: Artificial sequence
<220> FEATURE:
<223> OTHER INFORMATION: Peroxygenase motif III
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: The amino acid may be Gln or Glu.
<220> FEATURE:
<221> NAME/KEY: VARIANT
<222> LOCATION: (7)..(7)
<223> OTHER INFORMATION: The amino acid may be Asp, Glu or Gln.
<220> FEATURE:
<221> NAME/KEY: VARIANT
<222> LOCATION: (9)..(9)
<223> OTHER INFORMATION: The amino acid may be Ile or Met.

<400> SEQUENCE: 42

Arg Xaa Xaa Arg Ile Xaa Xaa Ser Xaa Ala Thr Asn
1               5                   10

<210> SEQ ID NO 43
<211> LENGTH: 10
<212> TYPE: PRT
<213> ORGANISM: Artificial sequence
<220> FEATURE:
<223> OTHER INFORMATION: Peroxygenase motif IV
<220> FEATURE:
<221> NAME/KEY: VARIANT
<222> LOCATION: (2)..(2)
<223> OTHER INFORMATION: The amino acid may be Ile or Met.
<220> FEATURE:
<221> NAME/KEY: VARIANT
<222> LOCATION: (6)..(6)
<223> OTHER INFORMATION: The amino acid may be Pro or Gly.
<220> FEATURE:
<221> NAME/KEY: VARIANT
<222> LOCATION: (7)..(7)
```

```
<223> OTHER INFORMATION: The amino acid may be Glu, Gln or Asn.
<220> FEATURE:
<221> NAME/KEY: VARIANT
<222> LOCATION: (8)..(8)
<223> OTHER INFORMATION: The amino acid may be Phe or Met.
<220> FEATURE:
<221> NAME/KEY: VARIANT
<222> LOCATION: (9)..(9)
<223> OTHER INFORMATION: The amino acid may be Ser, Asp or Asn.
<220> FEATURE:
<221> NAME/KEY: VARIANT
<222> LOCATION: (10)..(10)
<223> OTHER INFORMATION: The amino acid may be Phe or Leu.

<400> SEQUENCE: 43

Ser Xaa Ala Thr Asn Xaa Xaa Xaa Xaa Xaa
 1               5                  10

<210> SEQ ID NO 44
<211> LENGTH: 7
<212> TYPE: PRT
<213> ORGANISM: Artificial sequence
<220> FEATURE:
<223> OTHER INFORMATION: Peroxygenase motif V
<220> FEATURE:
<221> NAME/KEY: VARIANT
<222> LOCATION: (2)..(2)
<223> OTHER INFORMATION: The amino acid may be Pro, Asp or Lys.
<220> FEATURE:
<221> NAME/KEY: VARIANT
<222> LOCATION: (3)..(3)
<223> OTHER INFORMATION: The amino acid may be Asp or Gly.
<220> FEATURE:
<221> NAME/KEY: VARIANT
<222> LOCATION: (5)..(5)
<223> OTHER INFORMATION: The amino acid may be His, Phe or Trp.
<220> FEATURE:
<221> NAME/KEY: VARIANT
<222> LOCATION: (7)..(7)
<223> OTHER INFORMATION: The amino acid may be Ala or Pro.

<400> SEQUENCE: 44

Pro Xaa Xaa Phe Xaa Arg Xaa
 1               5

<210> SEQ ID NO 45
<211> LENGTH: 11
<212> TYPE: PRT
<213> ORGANISM: Artificial sequence
<220> FEATURE:
<223> OTHER INFORMATION: Peroxygenase motif VI
<220> FEATURE:
<221> NAME/KEY: VARIANT
<222> LOCATION: (1)..(1)
<223> OTHER INFORMATION: The amino acid may be Thr or Ile.
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: The amino acid may be Thr or Lys.
<220> FEATURE:
<221> NAME/KEY: VARIANT
<222> LOCATION: (11)..(11)
<223> OTHER INFORMATION: The amino acid may be Gly or Val.

<400> SEQUENCE: 45

Xaa Xaa Xaa Xaa Leu Tyr Pro Asn Pro Xaa Xaa
 1               5                  10

<210> SEQ ID NO 46
<211> LENGTH: 40
```

```
<212> TYPE: DNA
<213> ORGANISM: Artificial sequence
<220> FEATURE:
<223> OTHER INFORMATION: Primer AaP1F

<400> SEQUENCE: 46
acacaactgg ggatccacca tgaaatactt cagcctgttc                              40

<210> SEQ ID NO 47
<211> LENGTH: 36
<212> TYPE: DNA
<213> ORGANISM: Artificial sequence
<220> FEATURE:
<223> OTHER INFORMATION: Primer AaP1R

<400> SEQUENCE: 47
agatctcgag aagcttaatc tcgcccgtac gggaat                                  36

<210> SEQ ID NO 48
<211> LENGTH: 41
<212> TYPE: DNA
<213> ORGANISM: Artificial sequence
<220> FEATURE:
<223> OTHER INFORMATION: Primer AaP2F

<400> SEQUENCE: 48
acacaactgg ggatccacca tgaaatattt tcccctgttc c                            41

<210> SEQ ID NO 49
<211> LENGTH: 36
<212> TYPE: DNA
<213> ORGANISM: Artificial sequence
<220> FEATURE:
<223> OTHER INFORMATION: Primer AaP2R

<400> SEQUENCE: 49
agatctcgag aagcttaatc tcgcccgtat gggaag                                  36

<210> SEQ ID NO 50
<211> LENGTH: 39
<212> TYPE: DNA
<213> ORGANISM: Artificial sequence
<220> FEATURE:
<223> OTHER INFORMATION: Forward Primer

<400> SEQUENCE: 50
acacaactgg ggatccacca tggctcgcct tactttcct                               39

<210> SEQ ID NO 51
<211> LENGTH: 38
<212> TYPE: DNA
<213> ORGANISM: Artificial sequence
<220> FEATURE:
<223> OTHER INFORMATION: Reverse primer

<400> SEQUENCE: 51
agatctcgag aagcttactt tccataaggg aagatctg                                38

<210> SEQ ID NO 52
<211> LENGTH: 39
<212> TYPE: DNA
<213> ORGANISM: Artificial sequence
<220> FEATURE:
<223> OTHER INFORMATION: Forward primer

<400> SEQUENCE: 52
acacaactgg ggatccacca tgatctcgac ctcgaagca                               39
```

<210> SEQ ID NO 53
<211> LENGTH: 35
<212> TYPE: DNA
<213> ORGANISM: Artificial sequence
<220> FEATURE:
<223> OTHER INFORMATION: Reverse primer

<400> SEQUENCE: 53
agatctcgag aagcttaatc actcttgccc caggg                         35

<210> SEQ ID NO 54
<211> LENGTH: 38
<212> TYPE: DNA
<213> ORGANISM: Artificial sequence
<220> FEATURE:
<223> OTHER INFORMATION: Forward primer

<400> SEQUENCE: 54
acacaactgg ggatccacca tggtttcgtg caagctcc                      38

<210> SEQ ID NO 55
<211> LENGTH: 37
<212> TYPE: DNA
<213> ORGANISM: Artificial sequence
<220> FEATURE:
<223> OTHER INFORMATION: Reverse primer

<400> SEQUENCE: 55
agatctcgag aagcttacag tgtaccatac ggtttca                       37

<210> SEQ ID NO 56
<211> LENGTH: 38
<212> TYPE: DNA
<213> ORGANISM: Artificial sequence
<220> FEATURE:
<223> OTHER INFORMATION: Forward primer

<400> SEQUENCE: 56
acacaactgg ggatccacca tgaacggtct gttcgcca                      38

<210> SEQ ID NO 57
<211> LENGTH: 36
<212> TYPE: DNA
<213> ORGANISM: Artificial sequence
<220> FEATURE:
<223> OTHER INFORMATION: Reverse primer

<400> SEQUENCE: 57
agatctcgag aagcttagtt acgtccgtag gggaac                        36

<210> SEQ ID NO 58
<211> LENGTH: 38
<212> TYPE: DNA
<213> ORGANISM: Artificial sequence
<220> FEATURE:
<223> OTHER INFORMATION: Forward primer

<400> SEQUENCE: 58
acacaactgg ggatccacca tgctcaaacc gcgtgttc                      38

<210> SEQ ID NO 59
<211> LENGTH: 37
<212> TYPE: DNA

```
<213> ORGANISM: Artificial sequence
<220> FEATURE:
<223> OTHER INFORMATION: Reverse primer

<400> SEQUENCE: 59
agatctcgag aagcttaatc gtgtccgtaa gggaaaa                                    37
```